US010286020B2

(12) United States Patent
Shin et al.

(10) Patent No.: US 10,286,020 B2
(45) Date of Patent: May 14, 2019

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 156 days.

(21) Appl. No.: 15/304,414

(22) PCT Filed: Apr. 14, 2015

(86) PCT No.: PCT/KR2015/003703
§ 371 (c)(1),
(2) Date: Oct. 14, 2016

(87) PCT Pub. No.: WO2015/160164
PCT Pub. Date: Oct. 22, 2015

(65) Prior Publication Data
US 2017/0189459 A1    Jul. 6, 2017

(30) Foreign Application Priority Data

Apr. 15, 2014  (KR) .................. 10-2014-0044994

(51) Int. Cl.
| | | |
|---|---|---|
| *C12N 7/00* | (2006.01) | |
| *A61K 35/76* | (2015.01) | |
| *A23K 20/195* | (2016.01) | |
| *A23K 10/18* | (2016.01) | |
| *A23K 20/153* | (2016.01) | |
| *A23K 50/70* | (2016.01) | |
| *A23K 50/75* | (2016.01) | |

(52) U.S. Cl.
CPC ............. *A61K 35/76* (2013.01); *A23K 10/18* (2016.05); *A23K 20/153* (2016.05); *A23K 20/195* (2016.05); *A23K 50/70* (2016.05); *A23K 50/75* (2016.05); *C12N 7/00* (2013.01); *C12N 2795/10321* (2013.01); *C12N 2795/10333* (2013.01)

(58) Field of Classification Search
None
See application file for complete search history.

(56) References Cited

U.S. PATENT DOCUMENTS 6,942,858 B1    9/2005    Ghanbari et al.

FOREIGN PATENT DOCUMENTS

| | | |
|---|---|---|
| KR | 10-2011-0041670 A | 4/2011 |
| KR | 10-2012-0013149 A | 2/2012 |
| KR | 10-1275263 B1 | 6/2013 |
| KR | 10-1299179 B1 | 8/2013 |
| KR | 10-1381793 B1 | 4/2014 |
| WO | 2013/157813 A1 | 10/2013 |

OTHER PUBLICATIONS

Cheiljedang Corporation, KR 10-1299179, 2003, machine translation.*
Huff et al., Avian Diseases, 47:1399-1405, 2003.*
Kwon et al., KR 10-1275263, machine translation, 2013.*
Jamalludeen et al., Veterinary Microbiology, vol. 124 (2007) pp. 47-57.*
International Search Report dated Jun. 30, 2015 of PCT/KR2015/003703 which is the parent application and its English translation—4 pages.
Extended European Search Report dated Aug. 7, 2017 of corresponding European Patent Application No. 15779385.2—9 pages.
Jamalludeen et al., "Isolation and characterization of virulent bacteriophages against *Escherichia coli* serogroups O1, O2, and O78", Poultry Science, vol. 88, 2009, pp. 1694-1702.
Huff et al., "Method of administration affects the ability of bacteriophage to prevent colibacillosis in 1-day-old broiler chickens", Poultry Science, vol. 92, 2013, pp. 930-934.
Jamalludeen, "Isolation and characterization of lytic bacteriophages against *Escherichia coli* serogroups O1, O2, end O78", Proceeding of the Eleventh Veterinary Scientific Conference, 2012, pp. 56-63.
Tsonos et al., "A cocktail of in vitro efficient phages is not a guarantee for in vivo therapeutic results against avian colibacillosis", Veterinary Microbiology, vol. 171, Jul. 2014, pp. 470-479.
Lau et al., "Efficacy of a bacteriophage isolated from chickens as a therapeutic agent for colibacillosis in broiler chickens, " Poultry Science, vol. 89, 2010, pp. 2589-2596.
Oliveira et al., "Isolation and characterization of bacteriophages for avian pathogenic *E. coil* strains", Journal of Applied Microbiology, vol. 106, 2009, pp. 1919-1927.

* cited by examiner

*Primary Examiner* — Irene Marx
(74) *Attorney, Agent, or Firm* — Knobbe Martens Olson & Bear LLP

(57) ABSTRACT

The present invention relates to a novel bacteriophage ΦCJ24 (KCCM11462P) and a composition comprising the same as an active component. In addition, the present invention relates to a method for preventing and/or treating infectious diseases caused by avian pathogenic *E. coli* of birds by using the bacteriophage ΦCJ24 (KCCM11462P) or the composition.

3 Claims, 3 Drawing Sheets
Specification includes a Sequence Listing.

[Fig. 1]
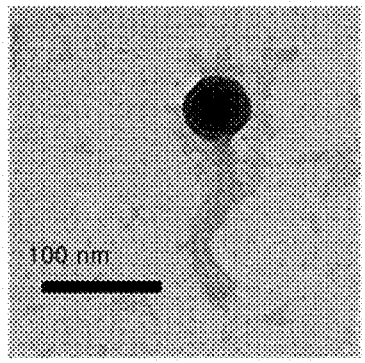
[Fig. 2]
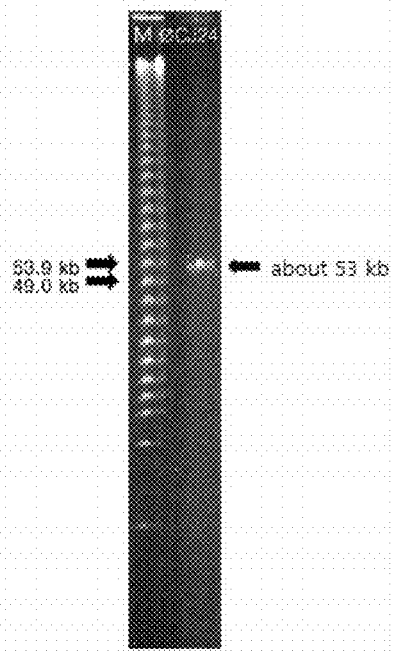

[Fig. 3]
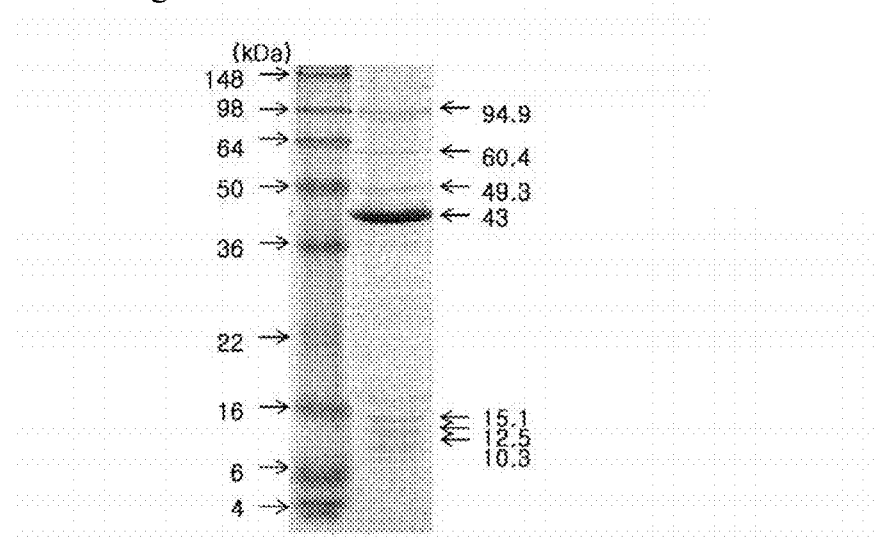
[Fig. 4]
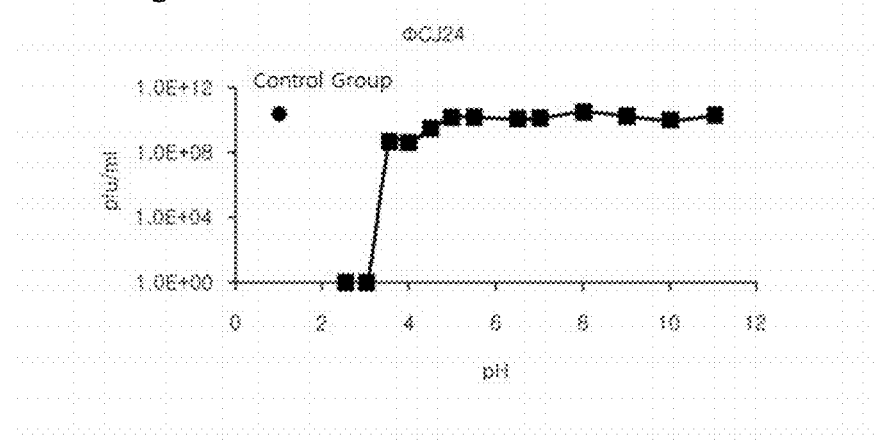

[Fig. 5]
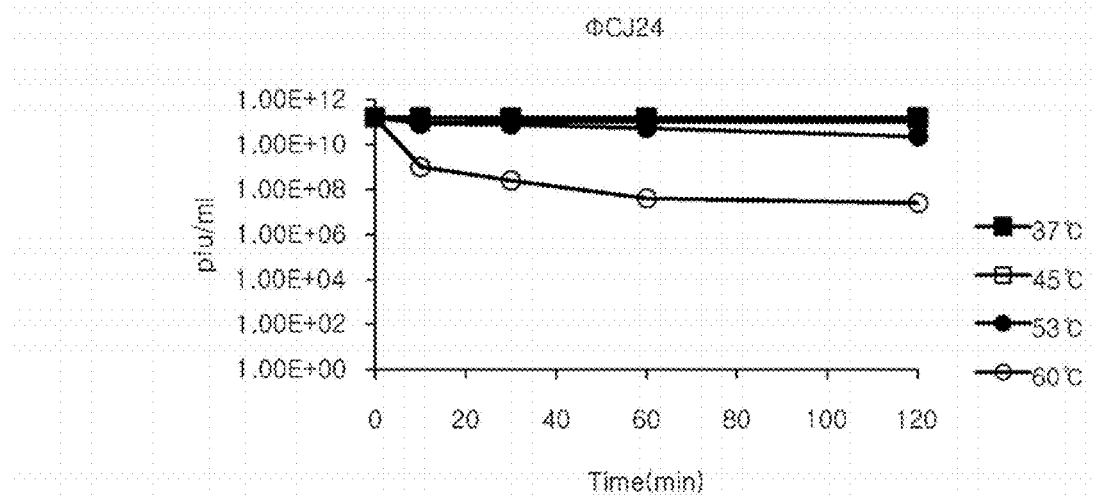
[Fig. 6]
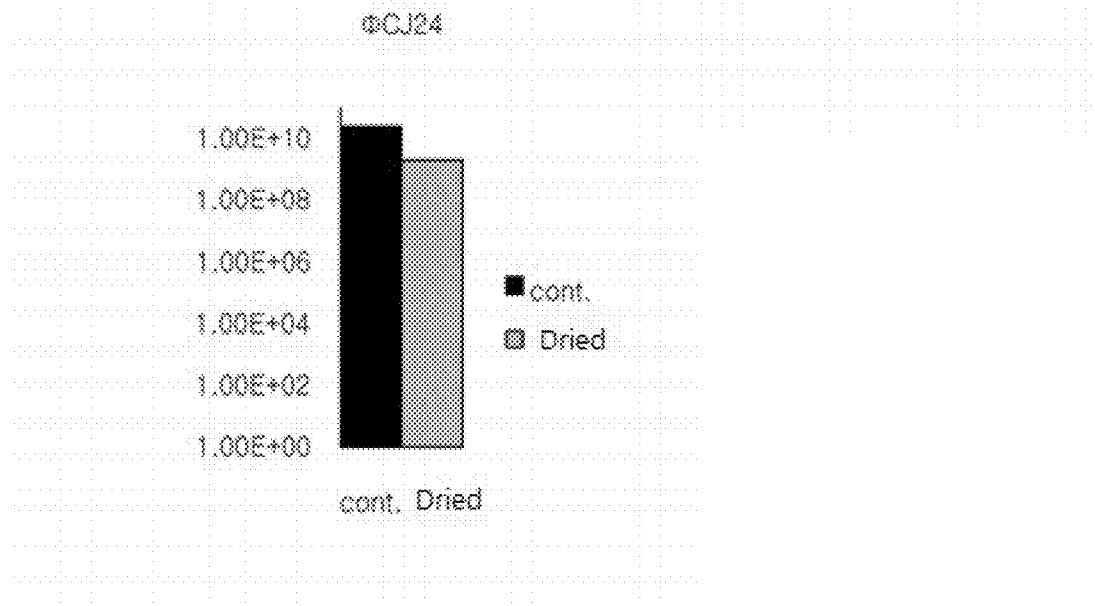

BACTERIOPHAGE AND COMPOSITION COMPRISING SAME

REFERENCE TO SEQUENCE LISTING

This application incorporates by reference the sequence listing submitted as ASCII text filed via EFS-Web Oct. 14, 2016, and updated by a file entitled "24332351_1_ST25.txt" created and last modified on Dec. 30, 2016, which is 77,326 bytes in size. The information in the electronic format of the Sequence Listing is incorporated herein by reference in its entirety.

TECHNICAL FIELD

The present invention relates to a novel bacteriophage having a specific ability to kill avian pathogenic *Escherichia coli* (APEC), a composition including the same, and a method for preventing or treating infectious diseases of birds using the novel bacteriophage or the composition.

BACKGROUND ART

*Escherichia coli* (hereinafter also referred to as *E. coli*) is a Gram-negative, short rod bacterium of genus *Escherichia*, family Enterobacteriaceae, and one of normal flora found in intestines of various animals including mammals. Most strains of *Escherichia coli* are non-pathogenic and can cause opportunistic infection, but some highly pathogenic strains cause various intestinal diseases and sepsis in animals including humans.

Among these strains of *Escherichia coli*, avian pathogenic *E. coli* (APEC) causes infection through the respiratory tract of birds such as chickens, geese, turkeys, and the like, and is known to pass into the avian body through the respiratory mucous membrane. Avian pathogenic *E. coli* causes diseases mostly in poultry with respect to respiratory diseases in birds, which leads to enormous economic damage in the poultry industry.

A bacteriophage refers to a bacterium specific virus that prevents and inhibits growth of a bacterium infected with a specific bacteriophage. As bacteriophages have stronger host specificity than antibiotics, and recent emergence of bacteria resistant to antibiotics and residual antibiotics in animals are growing problems, application of bacteriophages has drawn great interest.

Studies on bacteriophages have been actively performed in many countries, and there has been an increasing tendency to obtain approval from the Food and Drug Administration (FDA) for compositions using bacteriophages in addition to patent applications for bacteriophages.

However, bacteriophage related technologies for prevention and/or treatment of infectious diseases, which are important issues in the aviculture industry including poultry farming, due to avian pathogenic *Escherichia coli* are still insufficient, and therefore, there is a need for such bacteriophages and development of relevant technologies.

DISCLOSURE

Technical Problem

As a result of earnest investigation aimed at overcoming the emergence of bacteria resistant to antibiotics and residual antibiotics in animals and at effectively preventing and treating infectious diseases of birds, the present inventors isolated a novel bacteriophage ΦCJ24 (KCCM11462P) having a specific ability to kill avian pathogenic *Escherichia coli* causing respiratory diseases of poultry from natural sources.

In addition, the present inventors identified morphological, biochemical, and genetic properties of the novel bacteriophage, confirmed that the bacteriophage has excellent acid resistance, heat resistance, and drying resistance, and developed antibiotics, disinfectants, additives for feeds, and other compositions using the bacteriophage, a composition for preventing or treating infectious diseases in birds, and a method for preventing or treating diseases using the same.

It is an object of the present invention to provide a novel bacteriophage ΦCJ24 (KCCM11462P) having a specific ability to kill avian pathogenic *Escherichia coli*.

It is another object of the present invention to provide a composition for preventing and/or treating infectious diseases caused by avian pathogenic *Escherichia coli*, including the bacteriophage ΦCJ24 (KCCM11462P) as an active ingredient.

It is a further object of the present invention to provide antibiotics, additives for feeds, additives for drinking water, feeds, drinking water, disinfectants or detergents, including the bacteriophage ΦCJ24 (KCCM11462P) as an active ingredient.

It is yet another object of the present invention to provide a method for preventing and/or treating infectious diseases caused by avian pathogenic *Escherichia coli* using the bacteriophage ΦCJ24 (KCCM11462P) or the composition including the bacteriophage ΦCJ24 (KCCM11462P) as an active ingredient.

Technical Solution

One aspect of the present invention provides a novel bacteriophage ΦCJ24 (KCCM11462P) having a specific ability to kill avian pathogenic *Escherichia coli*.

Another aspect of the present invention provides a composition for preventing or treating infectious diseases caused by avian pathogenic *Escherichia coli*, including the bacteriophage ΦCJ24 (KCCM11462P) as an active ingredient.

A further aspect of the present invention provides antibiotics, additives for feeds, additives for drinking water, feeds, drinking water, disinfectants or detergents, including the bacteriophage ΦCJ24 (KCCM11462P) as an active ingredient.

Yet another aspect of the present invention provides a method for preventing or treating infectious diseases caused by avian pathogenic *Escherichia coli*, including: administering the bacteriophage ΦCJ24 (KCCM11462P) or the composition including the bacteriophage ΦCJ24 (KCCM11462P) as an active ingredient to birds.

Advantageous Effects

The bacteriophage ΦCJ24 (KCCM11462P) according to the present invention has an effect of having a specific ability to kill avian pathogenic *Escherichia coli*.

Further, the bacteriophage ΦCJ24 (KCCM11462P) according to the present invention has excellent acid resistance, heat resistance, and drying resistance, and thus can be employed not only as an agent for preventing or treating infectious diseases caused by avian pathogenic *Escherichia coli* at various ranges of temperature, pH, and dry conditions but also as antibiotics, additives for feeds, additives for drinking water, feeds, drinking water, disinfectants, detergents, and the like, including the bacteriophage ΦCJ24 (KCCM11462P) as an active ingredient.

Further, the present invention provides the bacteriophage ΦCJ24 (KCCM11462P) or antibiotics including the same as an active ingredient, and the antibiotics have effects in that the antibiotics have specificity for avian pathogenic *Escherichia coli* as compared to prior antibiotics and thus selectively kill specific pathogenic bacteria without killing beneficial bacteria; and that the antibiotics do not induce antibiotic resistance, resulting in extension of lifetime of products as compared to prior antibiotics.

Further, the present invention has effects of preventing or treating infectious diseases caused by avian pathogenic *Escherichia coli* by administering the bacteriophage ΦCJ24 (KCCM11462P) or the composition including the bacteriophage ΦCJ24 (KCCM11462P) as an active ingredient to birds.

DESCRIPTION OF DRAWINGS

FIG. 1 is an electron microscope image of a novel bacteriophage ΦCJ24 (KCCM11462P) (hereinafter referred to as 'ΦCJ24').

FIG. 2 shows results of pulsed field gel electrophoresis (PFGE) of a novel bacteriophage ΦCJ24.

FIG. 3 shows results of sodium dodecyl sulfate polyacrylamide gel electrophoresis (SDS-PAGE) of a novel bacteriophage ΦCJ24.

FIG. 4 is a graph depicting results of acid resistance experiment of a novel bacteriophage ΦCJ24.

FIG. 5 is a graph depicting results of heat resistance experiment of a novel bacteriophage ΦCJ24.

FIG. 6 is a graph depicting results of drying resistance experiment of a novel bacteriophage ΦCJ24.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ24 (KCCM11462P) (hereinafter referred to as 'ΦCJ24') having a specific ability to kill avian pathogenic *Escherichia coli* (APEC).

Avian pathogenic *Escherichia coli* refers to *Escherichia coli* that is transmitted through the respiratory tract of birds such as chickens, geese, turkeys, and the like, and that can cause infectious diseases of birds, specifically avian colibacillosis. Specifically, avian pathogenic *Escherichia coli* penetrates into the body of birds through the mucous membrane of the respiratory tract, and causes various diseases such as sepsis, granuloma, air sacculitis, salpingitis, arthritis, and the like. Avian pathogenic *Escherichia coli* is a Gram-negative bacillus just like general *Escherichia coli*, has peritrichous flagella for motility, and is an aerobic or facultative anaerobic bacterium which decomposes lactose and fructose to generate acids and gases.

Avian pathogenic *Escherichia coli* grows well on common media and is capable of growing at a temperature of about 7° C. to about 48° C. with ideal growth temperature ranging from about 35° C. to about 37° C. Specifically, at around 42° C. which is close to body temperature of birds, expression of pathogenic factors is effectively performed. Further, avian pathogenic *Escherichia coli* can grow at pH ranging from pH 4.5 to pH 9.0.

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Specifically, the bacteriophage ΦCJ24 according to the embodiment of the present invention is a bacteriophage that has species specificity of selectively infecting avian pathogenic *Escherichia coli* and morphologically belongs to morphotype B1 Siphoviridae having an icosahedral capsid and a long non-contractile tail (see FIG. 1). Homology between a nucleotide sequence of the bacteriophage ΦCJ24 and decoded nucleotide sequences of other bacteriophages is compared and results are shown in Table 1. The bacteriophage ΦCJ24 shows stable acid resistance at pH 3.5 to pH 11.0 without losing activity (FIG. 4), and in terms of heat resistance, the bacteriophage ΦCJ24 shows activity decline of about 1 log or less when exposed to 50° C. or more for two hours (FIG. 5). In terms of drying resistance, the bacteriophage ΦCJ24 shows activity decline of about 1 log when dried at 60° C. for two hours (FIG. 6). Partial DNA nucleotide sequences of the bacteriophage ΦCJ24 are set forth in SEQ ID NOs: 1 and 2 of Sequence List.

The bacteriophage ΦCJ24 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11462P.

Another embodiment of the present invention provides a composition for preventing or treating infectious diseases caused by avian pathogenic *Escherichia coli*, including the bacteriophage ΦCJ24 as an active ingredient.

Since the bacteriophage ΦCJ24 exhibits antibacterial activity capable of specifically killing avian pathogenic *Escherichia coli*, the bacteriophage ΦCJ24 can be utilized in prevention or treatment of diseases caused by infection with avian pathogenic *Escherichia coli*. Examples of infectious diseases caused by avian pathogenic *Escherichia coli* include avian colibacillosis, without being limited thereto.

Herein, the term "avian colibacillosis" refers to a disease occurring in the respiratory tract of birds due to infection with pathogenic *Escherichia coli*, and symptoms thereof include air sacculitis, perihepatitis, peritonitis, pericarditis, salpingitis, omphalitis, osteomyelitis or septicemia, thereby causing growth delay and mortality of infected birds.

Herein, the term "preventing" or "prevention" refers to all actions to inhibit the diseases or delay occurrence of the diseases by administering the bacteriophage ΦCJ24 and/or the composition including the bacteriophage ΦCJ24 as an active ingredient to an animal.

Herein, the term "treating" or "treatment" refers to all actions to improve or ameliorate symptoms of infectious diseases by administering the bacteriophage ΦCJ24 and/or the composition including the bacteriophage ΦCJ24 as an active ingredient to an animal.

The composition for preventing or treating infectious diseases caused by avian pathogenic *Escherichia coli* according to this embodiment may include the bacteriophage ΦCJ24 in amounts of $5 \times 10^2$ pfu/ml to $5 \times 10^{12}$ pfu/ml, specifically, $1 \times 10^6$ pfu/ml to $1 \times 10^{10}$ pfu/ml.

The composition for preventing or treating infectious diseases caused by avian pathogenic *Escherichia coli* according to this embodiment may further include pharmaceutically acceptable carriers, and may be formulated with the carriers to provide foods, medicines, additives for feeds or additives for drinking water, and the like. Herein, the term "pharmaceutically acceptable carriers" refers to carriers or diluents that do not stimulate an organism and do not inhibit biological activity and properties of administered compounds.

Types of carriers applicable to this embodiment are not particularly limited and any pharmaceutically acceptable carriers commonly used in the art may be utilized. Examples of the carriers may include saline, distilled water, Ringer's solution, buffered saline, an albumin injection solution, a dextrose solution, a maltodextrin solution, glycerol, and ethanol, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, granules, and tablets.

Methods for administering the composition for preventing or treating infectious diseases caused by avian pathogenic *Escherichia coli* according to this embodiment are not particularly limited, and any methods commonly used in the related art may be used. One example of the administration method may include oral administration or parenteral administration.

Examples of dosage forms for oral administration may include troches, lozenges, tablets, water soluble suspensions, oil-based suspensions, formulated powder, granules, emulsions, hard capsules, soft capsules, syrups, or elixirs, and the like.

In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by avian pathogenic *Escherichia coli* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ24 as an active ingredient.

Herein, the term "antibiotics" refers to a preparation that is administered to animals including humans in medicine form and exhibits efficacy of sterilizing bacteria, and is used as a general term for antiseptics, germicides and antibacterial agents.

Antibiotics of this embodiment including the bacteriophage ΦCJ24 as an active ingredient have effects in that the antibiotics have specificity for avian pathogenic *Escherichia coli* as compared to typical antibiotics and thus kill specific pathogenic bacteria, but not beneficial bacteria; and in that the antibiotics do not induce drug resistance, causing extension of lifetime of products as compared to typical antibiotics.

Yet another embodiment of the present invention provides an additive for avian feeds or avian drinking water, which includes the bacteriophage ΦCJ24 as an active ingredient.

Birds as a subject to which the additives for avian feeds or the additives for avian drinking water are applied are not particularly limited, but birds in this embodiment are particularly poultry.

Herein, poultry is a generic name for animals belonging to birds among livestock. Poultry is not particularly limited, and may comprise at least one selected from the group consisting of chickens, geese, turkeys, and the like.

The additives for avian feeds or the additives for avian drinking water may be used by separately preparing additives for feeds or additives for avian drinking water using the bacteriophage ΦCJ24 or the composition including the same and mixing feeds or drinking water with the additives, or directly adding the bacteriophage ΦCJ24 or the composition including the same in a process of preparing feeds or drinking water.

The bacteriophage ΦCJ24 or the composition including the bacteriophage ΦCJ24 as an active ingredient used in the form of additives for feeds or additives for drinking water according to this embodiment may be a liquid form or a dried form, for example, a dried powder form.

For example, the bacteriophage ΦCJ24 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. The microorganisms may be selected from the group consisting of *Bacillus* sp. such as *Bacillus subtilis* capable of producing proteases, lipases and/or glycosyltransferase s; lactic acid bacteria such as

*Lactobacillus* sp. having physiological activity and organic material decomposing capability under anaerobic conditions like the stomach of cattle; filamentous bacteria such as Aspergillus oryzae having effects of weight gain in animals, increase in milk production, and increase of digestion-absorption rate of feeds; and yeasts such as *Saccharomyces cerevisiae* and the like. These microorganisms may be used alone or in combination thereof.

The additives for feeds or additives for drinking water according to this embodiment including the bacteriophage ΦCJ24 as an active ingredient may further include other additives as needed. Examples of usable additives may include binders, emulsifiers, and preservatives added for prevention of quality deterioration of feeds or drinking water; amino acid, vitamin, enzyme, probiotics, flavoring agents, non-protein nitrogen compounds, silicate, buffering agents, coloring agents, extracting agents or oligosaccharides that are added in order to increase utility of feeds or drinking water; and other supplements to feeds, and the like. These additives may be used alone or in combination thereof.

The additives for feeds according to the present invention may be present in amounts of 0.05 parts by weight to 10 parts by weigh, specifically 0.1 parts by weight to 2 parts by weight, based on 100 parts by weight of feeds. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ24 against avian pathogenic *Escherichia coli* to be sufficiently displayed.

Yet another embodiment of the present invention provides feeds or drinking water prepared by adding the additives for feeds or the additives for drinking water including the bacteriophage ΦCJ24 as an active ingredient to feeds or drinking water, or directly adding the bacteriophage ΦCJ24 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grain, and the like; and animal feeds such as proteins, inorganic substances, oils and fats, minerals, single cell proteins, and animal planktons or foods. These feeds are used alone or in combination thereof.

Drinking water used in this embodiment is not particularly limited, and any drinking water commonly used in the related art may be used.

Yet another embodiment of the present invention provides disinfectants or detergents including the bacteriophage ΦCJ24 as an active ingredient. Dosage forms of the disinfectants or detergents are not particularly limited, and any dosage forms commonly used in the related art may be used.

In order to remove avian pathogenic *Escherichia coli*, the disinfectants may be sprayed to habitats of birds, slaughterhouses, dead regions, kitchens, and cooking equipment, without being limited thereto.

The detergents may be used to wash a surface of the dermis or body parts of birds that are exposed to or can be exposed to avian pathogenic *Escherichia coli*, without being limited thereto.

Yet another embodiment of the present invention provides a method for preventing or treating infectious diseases caused by avian pathogenic *Escherichia coli* using the bacteriophage ΦCJ24 or the composition including the bacteriophage ΦCJ24 as an active ingredient.

Specifically, the prevention method or treatment method of this embodiment includes administering a pharmaceutically effective amount of the bacteriophage ΦCJ24 or the composition including the bacteriophage ΦCJ24 as an active ingredient to birds that are exposed to or can be exposed to avian pathogenic *Escherichia coli*. Suitable total amounts of the bacteriophage ΦCJ24 or the composition including the same per day may be determined by a physician within proper medicinal judgment, as apparent to those skilled in the art.

A concrete pharmaceutically effective amount of the bacteriophage ΦCJ24 or the composition including the bacteriophage ΦCJ24 as an active ingredient to certain birds may be determined by taking into account the sorts and degree of reaction to achieve, age, body weight, general health condition, sex or diet of corresponding individuals, administration time and administration routes of bacteriophage ΦCJ24 or a composition including the same, and secretion rate of the composition, treatment period, and the like, and may differ depending upon various factors and similar factors well known in the field of medicine including ingredients of medicines that are used simultaneously or at different times.

The bacteriophage ΦCJ24 or the composition including the bacteriophage ΦCJ24 as an active ingredient may be administered in the form of a pharmaceutical preparation to birds by intranasal spraying, or directly added to avian feeds or drinking water so as to be digested, and may be mixed in the form of additives for feeds or additives for drinking water with feeds or drinking water and then administered.

Routes and methods for administration of the bacteriophage ΦCJ24 or the composition including the bacteriophage ΦCJ24 as an active ingredient are not particularly limited, and the administration may be realized by any routes and methods so long as the administration allows the bacteriophage ΦCJ24 or the composition including the same to reach desired tissues. Namely, the bacteriophage ΦCJ24 or the composition including the bacteriophage ΦCJ24 as an active ingredient may be administered by various oral or parenteral routes, and examples of administration may include oral, rectal, topical, intravenous, intraperitoneal, intramuscular, intra-arterial, trans-dermal, intranasal, and inhalation, without being limited thereto.

Hereinafter, the present invention will be described in more detail with reference to a preferred example. It should be understood that these examples are not to be construed in any way as limiting the present invention.

EXAMPLE 1

Isolation of Bacteriophage that Infects Avian Pathogenic *Escherichia coli*

Example 1-1

Bacteriophage Screening and Single Bacteriophage Isolation 50 ml of a specimen obtained from chicken feces collected around a poultry farm in Chengwon-gun, Chungcheong Province was centrifuged at 4,000 rpm for 10 minutes, and the resulting supernatant was filtered through a 0.45 μm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 µl of a shaking culture solution ($OD_{600}$=2) of avian pathogenic *Escherichia coli* (E10-4) obtained from the Department of Veterinary Medicine of Konkuk University and 2 ml of 10×LB medium (10 g/l of tryptophan; 5 g/l of yeast extract; 10 g/l of NaCl) were mixed with 18 ml of the filtered specimen liquid, followed by culturing at 30° C. for 18 hours, and the resulting cultured solution was centrifuged at 4,000 rpm for 10 minutes, and the resulting supernatant was filtered through a 0.45 µm filter. Subsequently, a mixed solution consisting of 3 ml of 0.7% (w/v) agar and 150 µl of a shaking culture solution ($OD_{600}$=2) of avian pathogenic *Escherichia coli* (E10-4) was poured and solidified on an LB medium plate, to which 10 µl of the specimen liquid was added dropwise, followed by culturing at 30° C. for 18 hours, thereby identifying formation of plaques.

Since it is known that one sort of bacteriophage is present per plaque, the inventors tried to isolate single bacteriophages from the formed plaques. Specifically, 400 µl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution.

Subsequently, 100 µl of the bacteriophage solution was mixed with 12 ml of 0.7% (w/v) agar and 500 µl of a shaking culture solution ($OD_{600}$=2) of avian pathogenic *Escherichia coli* (E10-4), which was used to perform a soft agar overlay method using an LB medium plate having a diameter of 150 mm wherein cultivation was performed until the bacteriophage was completely lysed. After completion of cultivation, 15 ml of SM solution was added to the LB medium plate and left at room temperature for 4 hours, thereby obtaining a bacteriophage solution.

To the obtained solution, 1% (v/v) chloroform was added and mixed for 10 minutes, followed by centrifugation at 4,000 rpm for 10 minutes, thereby obtaining a supernatant, which in turn was filtered through a 0.45 µm filter, thereby obtaining a final specimen.

Example 1-2

Large Scale Culture and Purification of Bacteriophage

The bacteriophage obtained in Example 1-1 was cultured at large scale using avian pathogenic *Escherichia coli* (E10-4), and then the bacteriophage was purified therefrom.

Specifically, avian pathogenic *Escherichia coli* (E10-4) was shaking cultured, and inoculated at $1.0 \times 10^{10}$ cfu, followed by centrifuging at 4,000 rpm for 10 minutes, and re-suspending in 4 ml of SM solution. To this, the bacteriophage was added at $1.0 \times 10^6$ pfu with multiplicity of infection (MOI) of 0.0001, and then left at room temperature for 20 minutes.

Next, 150 ml of LB medium was inoculated therewith, and cultured at 30° C. for 6 hours. After completion of cultivation, chloroform was added to a volume of 1% (v/v) of the final volume, followed by stirring for 20 minutes, to which DNase I and RNase A as restriction enzymes were added in a final concentration of 1 µg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 4 ml of chloroform was added thereto with stirring, followed by centrifugation at 4° C. with 4,000 rpm for 20 minutes, thereby obtaining a supernatant. The supernatant was filtered through a 0.45 µm filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill avian pathogenic *Escherichia coli* from samples collected from chicken feces on farms, which was designated as "Bacteriophage ΦCJ24" and deposited at the Korean Culture Center of Microorganisms (KCCM) (361-221 Hongje 1-dong, Seodaemun-gu, Seoul, Korea) on Oct. 25, 2013 under accession number KCCM 11462P.

EXAMPLE 2

Morphology Observation of ΦCJ24

The bacteriophage ΦCJ24 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water.

Subsequently, the carbon film was mounted on a copper grid, and stained with 4% uranyl acetate for 60 seconds, dried, and examined under a transmission electron microscope (JEM-1011, 80 kV, magnification of ×200,000) (FIG. 1).

FIG. 1 is a transmission electron microscope image of bacteriophage ΦCJ24, in which the bacteriophage ΦCJ24 had morphological characteristics of an icosahedral capsid with a long non-contractile tail, indicating that the bacteriophage belongs to morphotype B1 Siphoviridae.

EXAMPLE 3

Total Genomic DNA Size Analysis of ΦCJ24

Genomic DNA was extracted from the bacteriophage ΦCJ24 purified in Example 1.

Specifically, to a cultured solution of the purified bacteriophage ΦCJ24, 20 mM ethylenediaminetetraacetic acid (EDTA), 50 µg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal amount of PC (phenol:chloroform=1:1), followed by centrifugation at room temperature and 12,000 rpm for 10 minutes, thereby obtaining a supernatant. The supernatant was mixed with an equal amount of chloroform, followed by centrifugation at room temperature and 12,000 rpm for 10 minutes, thereby obtaining a supernatant. The supernatant was mixed with 10% (v/v) of 3M sodium acetate based on the total volume, followed by the addition of 2 volumes of 95% cold ethanol, mixing, and standing at −20° C. for 1 hour.

Subsequently, the resulting substance was centrifuged at 0° C. and 12,000 rpm for 10 minutes, from which a supernatant was removed to obtain a precipitate, which was dissolved in 50 µl of TE buffered solution (Tris-EDTA, pH 8.0). The extracted DNA was diluted 10 fold, and then concentration of DNA was determined by measuring absorbance at $OD_{260}$.

Next, 1 µg of DNA was loaded on a 1% PFGE (pulsed field gel electrophoresis) agarose gel, and developed using BIORAD PFGE SYSTEM NO.7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ24, and it could be seen that the genomic DNA size of the bacteriophage ΦCJ24 was about 53 kbp.

EXAMPLE 4

Protein Pattern Analysis of ΦCJ24

15 μl of purified bacteriophage ΦCJ24 solution ($10^{11}$ pfu/ml titer) was mixed with 3 μl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ24, and it could be seen that main proteins had a size of about 10.3 kDa, about 12.5 kDa, about 15.1 kDa, about 43 kDa, about 49.3 kDa, about 60.4 kDa and about 94.9 kDa.

EXAMPLE 5

Analysis of Genetic Properties of ΦCJ24

In order to determine genetic properties of the bacteriophage ΦCJ24 purified in Example 1, DNA of the bacteriophage ΦCJ24 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterProScan program.

Nucleotide sequence of the bacteriophage ΦCJ24 showed similarity to nucleotide sequence of previously reported bacteriophages (*Escherichia* phage phiEB49, *Escherichia* phage KBN21), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ24 and decoded nucleotide sequence of the prior reported bacteriophage in the art.

TABLE 1

| Query | | | | Subject | Score | | Identities | |
|---|---|---|---|---|---|---|---|---|
| Name | Length | Start | End | Description | Bit | E-Value | Match/Total | Pct. (%) |
| SEQ ID NO: 1 | 50547 | 25529 | 27458 | *Escherichia* phage phiEB49, complete genome | 1283 | 0 | 1638/1959 | 83 |
| SEQ ID NO: 2 | 8358 | 4 | 8358 | *Escherichia* phage KBNP21, complete genome | 16360 | 0 | 8330/8355 | 99 |

DNA of the prepared bacteriophage ΦCJ24 was analyzed using a DNA sequencer and partial results of the analyzed nucleotide sequence are set forth in SEQ ID NOs: 1 and 2.

EXAMPLE 6 pH Stability of ΦCJ24

In order to identify whether the bacteriophage ΦCJ24 can maintain stability at low pH like stomach conditions, stability of the bacteriophage ΦCJ24 was examined at various pH (pH 2.5, 3.0, 3.5, 4.0, 5.5, 6.5, 7.0, 8.0, 9.0, 10.0 and 11.0).

For the experiment, various pH solutions (sodium acetate buffer solutions (pH 4.0, pH 4.5, pH 5.0, pH 5.5), sodium citrate buffer solutions (pH 2.5, pH 3.0 and pH 3.5), sodium phosphate buffer solutions (pH 6.5 and pH 7.0), and Tris-HCl solutions (pH 8.0, pH 9.0, pH 10.0 and pH 11.0) were prepared at a concentration of 0.2M.

180 μl of each pH solution was mixed with 20 μl of a bacteriophage solution with $2.0×10^{11}$ PFU/ml titer to allow each pH solution to have a concentration of 1M, and then the resulting solution was left at room temperature for 2 hours. For a control group, 20 μl of a bacteriophage solution with $2.0×10^{11}$ PFU/ml titer was mixed with 180 μl of SM solution by the same method, and the resulting solution was left at room temperature for 2 hours. Thereafter, the solutions were serially diluted, and 10 μl of each of solutions in each dilution step was cultured by the soft agar overlay method at 30° C. for 18 hours to determine bacteriophage titer based on whether the bacteriophage was lysed (FIG. 4).

FIG. 4 shows experimental results of acid resistance of the bacteriophage ΦCJ24. In FIG. 4, it could be seen that the bacteriophage ΦCJ24 did not lose its activity and maintained stability from pH 3.5 to pH 11.0, as compared with the control group.

EXAMPLE 7

Heat Stability of Bacteriophage ΦCJ24

If bacteriophages are formulated into additives for feeds among dosage forms of bacteriophages, heat can be generated during formulation procedures, and thus, the following experiment was performed in order to determine heat stability of bacteriophages.

Specifically, 100 μl of bacteriophage ΦCJ24 solution with $1.65×10^{11}$ PFU/ml was left at 37° C., 45° C., 53° C. and 60° C. for 10 minutes, 30 minutes, 60 minutes and 120 minutes, respectively. Thereafter, the resulting experimental culture solution was serially diluted, 10 μl of each of solutions in each dilution step was cultured by the soft agar overlay method at 30° C. for 18 hours to determine bacteriophage titer based on whether the bacteriophage was lysed (FIG. 5).

FIG. 5 shows experimental results of heat resistance of bacteriophage ΦCJ24. As shown in FIG. 5, it could be seen that bacteriophage ΦCJ24 showed activity loss of about 1 log or less until bacteriophage ΦCJ24 was exposed to 53° C. for 120 minutes, and activity decline was observed as time went by when bacteriophage ΦCJ24 was exposed to 60° C.

EXAMPLE 8

Drying Stability of Bacteriophage ΦCJ24

If bacteriophages are formulated into additives for feeds among dosage forms of bacteriophages, bacteriophages can be dried during formulation procedures, and thus, the following experiment was performed in order to determine stability of bacteriophages against drying conditions.

Based on the results from heat resistance experiment, drying experiment was performed using a SpeedVac concentrator. 200 μl of bacteriophage ΦCJ24 solution with $2.5×10^{10}$ PFU/ml was dried at 60° C. under vacuum for 2 hours, and the resulting pellets were introduced to 200 μl of SM solution, followed by completely re-suspending at 4° C. for one day, thereby measuring titers (FIG. 6).

As shown in FIG. 6, it could be seen that after drying, as compared with initial titers and relative stability, bacteriophage ΦCJ24 showed activity loss of about 1 log when bacteriophage ΦCJ24 was dried at 60° C. for 2 hours.

EXAMPLE 9

Examination of Infection Range of Bacteriophage ΦCJ24 on a Wild-Type Isolated Strain, Avian Pathogenic *Escherichia coli*

Lytic activity of bacteriophage ΦCJ24 was tested for 46 strains of the wild-type avian pathogenic *Escherichia coli* isolated by College of Veterinary Medicine, Konkuk University (KU), 10 strains of avian pathogenic *Escherichia coli* isolated by Korea Animal and Plant Quarantine Agency (KAPQA), 7 strains of avian pathogenic *Escherichia coli* isolated by College of Veterinary Medicine, Chonbuk National University (CNU), and 26 strains of disease-diagnosed avian pathogenic *Escherichia coli* isolated by Komipharm farm (KF) in addition to avian pathogenic *Escherichia coli* (E10-4) used in the present experiment.

Specifically, 150 μl of a shaking culture solution of each strain ($OD_{600}$=2) was mixed, and 10 μl of bacteriophage ΦCJ24 solution with $10^9$ pfu/ml titer was dropped thereto and cultured by the soft agar overlay method at 30° C. for 18 hours, and then plaque formation was examined (Table 2).

The results are shown in Table 2.

TABLE 2

| No. | KU strains | Sero-typing | ΦCJ24 |
|---|---|---|---|
| 1 | E09-1 | | |
| 2 | E09-2 | | |
| 3 | E09-3 | | 0 |
| 4 | E09-4 | | |
| 5 | E09-5 | | |
| 6 | E09-6 | O-78 | 0 |
| 7 | E09-7 | | |
| 8 | E09-8 | O-78 | 0 |
| 9 | E09-9 | O-78 | 0 |
| 10 | E09-10 | | |
| 11 | E09-11 | O-78 | 0 |
| 12 | E09-12 | O-125 | |
| 13 | E09-13 | | |
| 14 | E09-14 | | |
| 15 | E09-15 | | 0 |
| 16 | E09-16 | | |
| 17 | E09-17 | | |
| 18 | E09-18 | | |
| 19 | E09-19 | | |
| 20 | E09-20 | | |
| 21 | E09-21 | | |
| 22 | E09-22 | | |
| 23 | E09-23 | | 0 |
| 24 | E09-24 | | |
| 25 | E09-25 | | |
| 26 | E09-26 | | |
| 27 | E09-27 | | 0 |
| 28 | E09-28 | | |
| 29 | E09-29 | | |
| 30 | E09-30 | | 0 |
| 31 | E09-31 | | |
| 32 | E09-32 | | 0 |
| 33 | E09-33 | | |
| 34 | E09-34 | | 0 |
| 35 | E09-35(297) | O-78 | 0 |
| 36 | E09-36(343) | | |
| 37 | E09-37(343) | | |
| 38 | E09-38(343) | | |
| 39 | E09-39(353) | | |
| 40 | E09-40(353) | | |
| 41 | E09-41(376) | | |
| 42 | E09-42(376) | | |
| 43 | E10-2 | O-1 | 0 |
| 44 | E10-3 | O-78 | 0 |
| 45 | E10-4 | O-78 | 0 |
| 46 | E10-5 | O-78 | 0 |
| 47 | E10-6 | | |

| No. | KAPQA strains | Sero-typing | ΦCJ24 |
|---|---|---|---|
| 48 | 06Q-035 | O-78 | 0 |
| 49 | 06D-044 | O-78 | 0 |
| 50 | 06Q-140 | O-78 | 0 |
| 51 | 07D-001 | O-78 | 0 |
| 52 | 07D-022 | O-78 | 0 |
| 53 | 07Q-039 | O-78 | 0 |
| 54 | KWU-02 | O-78 | 0 |
| 55 | KWU-32 | O-78 | 0 |
| 56 | KWU-33 | O-78 | 0 |
| 57 | KWU-43 | O-78 | 0 |

| No. | CNU Strains | Sero-Typing | ΦCJ24 |
|---|---|---|---|
| 58 | A12-MRA-076-① | | |
| 59 | A10-LSf-005 | | |
| 60 | A11-LSF-043 | | |
| 61 | A12-MRA-076-② | | |
| 62 | D12-JW-058 | | |
| 63 | A12-LSF-083 | O-78 | 0 |
| 64 | A12-MRA-076-③ | | |

| No. | KF Strains | Sero-typing | ΦCJ24 |
|---|---|---|---|
| 65 | 12-001-3 | | |
| 66 | 12-053 | | |
| 67 | 12-055 | | |
| 68 | 12-086-1 | O-78 | 0 |
| 69 | 12-086-2 | O-78 | 0 |
| 70 | 12-096-3 | | |
| 71 | 12-175 | | |
| 72 | 12-187 | O-78 | 0 |
| 73 | 12-211-5 | | |
| 74 | 12-220-4 | | |
| 75 | 12-220-6 | | |
| 76 | 12-248 | | |
| 77 | 12-261-1 | | |
| 78 | 12-266 | | |
| 79 | 12-274-1 | | |
| 80 | 12-275-2 | O-78 | 0 |
| 81 | 12-286-2 | | |
| 82 | 12-300 | O-78 | 0 |
| 83 | 12-303-2 | O-78 | 0 |
| 84 | 12-304-3 | | |
| 85 | 12-299-1 | O-78 | 0 |
| 86 | 12-299-2 | O-78 | 0 |
| 87 | 12-299-3 | O-78 | 0 |
| 88 | 12-324 | O-78 | 0 |
| 89 | 12-338-1 | O-78 | 0 |
| 90 | 12-338-4 | O-78 | 0 |

As shown in table 2, the bacteriophage ΦCJ24 exhibits infection ability to avian pathogenic *Escherichia coli* (including O-1, O-78 serotypes), which are major causative bacteria of avian colibacillosis in general poultry farms.

It is known that O-78 serotype is generally the most dominant strain among avian pathogenic *Escherichia coli* isolated from poultry farms.

The invention claimed is:

1. A method for treating infectious diseases caused by avian pathogenic *Escherichia coli*, comprising:
   administering the bacteriophage ΦCJ24 (Accession No. KCCM11462P) to birds.

2. The method for preventing or treating infectious diseases caused by avian pathogenic *Escherichia coli* according to claim 1, wherein the infectious disease is avian colibacillosis.

3. A method for treating infectious diseases caused by avian pathogenic *Escherichia coli*, comprising:
   administering a composition comprising the bacteriophage ΦCJ24 (Accession No. KCCM11462P) to birds.

* * * * *

SEQUENCE LISTING

<160> NUMBER OF SEQ ID NOS: 2

<210> SEQ ID NO 1
<211> LENGTH: 50547
<212> TYPE: DNA
<213> ORGANISM: Artificial Sequence
<220> FEATURE:
<223> OTHER INFORMATION: Novel Bacteriophage CJ24

<400> SEQUENCE: 1

| | | | | | |
|---|---|---|---|---|---|
| ctcgtacact | cggattgatt | caagctgcgc | accttccttg | attggtgatg | tcaggagtcg | 60 |
| gttgtcacgg | acgacggcga | cgatggcgga | accaccataa | agccgctccc | atgagaacgc | 120 |
| ctcgacgatc | tgcttattca | gtttcatgcc | atcccaaagt | gatttgaatg | ctttctcatc | 180 |
| cttcacgccg | tcaaggccga | atccagggaa | aaccatttct | tctggaatca | catcgacaat | 240 |
| tttcttagcc | ataggatcat | caatgtaaaa | ctgcgtcacg | tacatctgat | cgtatagcga | 300 |
| tgcaagcgcg | ccgcctgccg | taccttcacc | cttaaacgtc | ttgttgtaag | agtctgtctt | 360 |
| aacgcttttt | ttactcatct | gtttttctcc | caataaaaaa | ggctaggttg | ttagcctagc | 420 |
| cattatacat | tatttgactt | ccgacttacc | atgattttca | tgatagccca | aagcgaactc | 480 |
| cgcagacttc | cttgcgcaaa | ctgcatcgaa | ccaatcagag | tagtatccca | atgacttcct | 540 |
| ctctcctttc | cctgagttac | ctatgaaagc | ccaccacttg | gatcttgaat | cataccagta | 600 |
| aacacctaca | cacccgcttt | tattccttac | tgacttcttt | gtgtttctac | cgttatcctt | 660 |
| atgggtaaca | acccttaaat | tctccctcct | attgtcgttc | cttatgtgat | ttttgtgatc | 720 |
| tatctgcatc | ccatcaggga | tatctccatt | atcgaattcc | catgcgaatc | tgtgagcaag | 780 |
| aagcgatacg | ccacctatcg | ttatcctcac | ataaccatca | gcatcaagtg | ttcccgctat | 840 |
| gtcaccaggg | tagaatttac | tcttttaat | cttgatcatc | cacctaacat | aaactccatc | 900 |
| atacgttaga | taattcttgg | ctatgtcata | aatatcgctt | cttgcattct | gcattacacc | 960 |
| cccctactta | atccggctaa | acgtttcatt | ctagacactg | gatcatccag | catgttcatc | 1020 |
| tcaaagttta | cagcatcaaa | tacgttatcg | caaatgtcat | catgaggaga | tgaatcatca | 1080 |
| aacgtaaatg | acaccaattc | aatctccatg | tcagaaagca | tctcatgaga | ttcagggaat | 1140 |
| acacaacgcc | cagccttcat | gattggtgct | gcgtccattg | cgcgagttac | cttatccgta | 1200 |
| tttcgctgaa | ctggcgtgat | gtcaatcggg | agcttcttgt | tgattgactg | gatcaggcca | 1260 |
| gtgccgctcg | ccttgtcttc | aatgtaaacc | ttgcgcagtg | aagtcttgtt | ctccttcgcc | 1320 |
| cacttgaagc | agttgctgta | aaaattaaga | gccatctttt | caagttccgg | cgcttcccac | 1380 |
| ttaccgcgaa | tgccgtcgat | gaaatatacg | cgatccttat | acttgcccca | caaaacaaag | 1440 |
| acgctgtagt | cgtgtatttc | ctctgctttc | tgcgctgtat | ccgcagtggt | gaacaggtat | 1500 |
| tcgaagcgat | ccggttttgg | catgtcggct | ttttcgccgt | ctccgtaata | ctggaaccag | 1560 |
| tccgatttaa | acgcgttgcc | gccaagcgcg | atgggcttct | gctgatactg | agattcaaac | 1620 |
| gtatacaggt | cagcttcgcg | caatgccagt | aggcttctg | cgctctcctt | cgcgggccag | 1680 |
| aaagaaaagt | gttcaacgcc | gtcaatcatt | accgatgggg | aggatagcac | gtctctgtca | 1740 |
| aattcctctt | tcaaccagtc | aggaagcgtg | tctctgtatt | cctcggttac | cagcgccggg | 1800 |
| atgattacct | gctcaaactg | catcccaccc | ataccgccat | tcatcaggaa | ccacgtcgca | 1860 |
| tcgtttacgt | gtagtcgctg | ctgaacaaca | acgcatggtg | tcttgtcatt | cattcttcgc | 1920 |
| gatcgaacgt | tgttctttaa | cagcgtgtga | ccagcctttc | tctttactgc | tgagtatagg | 1980 |
| tctttcggct | tctcagggtc | atcaagcgtc | agcattccgg | tgaagccatc | atccatataa | 2040 |

```
ccgccacgct taccagttac ctgaccaccg atcgcacgtg aagttagagt taaccatgcc    2100 tttteetttg agtttagagc ggtaatgtca ccacctgaag cctttgctag tttgcagggc    2160
caaagctcct ggaactcatc agacccgata atctcacgcg tcctgatccc gttatcctta    2220
acgagactat cagagaatga gaggttaaga ttccttatct tctcgctcct gaacatgcaa    2280
tacactggca tgtgaatgga gaagatctca gtcttgccag agcctggggt aatgttgaat    2340
atgatgtttt gtatctcacc gttgattatc tgctcaacct tccagcaaag gtagttgaag    2400
tgccaattag acctaaactt ttgagcctgt atcaaagcga accatatgcg cataaaatca    2460
ctaaaagacc tttcgctcat caccttcact accgacttct ctttctcggt tagatttttcc    2520 catattaaaa tgtctttact tgccattgtg cacatactcc acgtgaacta gctaaaggtt    2580
tatcaaattt tatcaagaac gcttttcaca gcatcctcaa tcgtctgagt atcattcact    2640
acattactta cgttgacctc ggcgggcttg tcgattccaa tctccttgcc tacaaaccca    2700
gcattgatga tattggctgc agcaagctga tattttttgct catggattac agagtcaacg    2760
aaccccatta cctccgcgaa tccaggtgat gcgcgccagc tctgaattga gcttgctgta    2820
actccgcagt acaggcagaa tccgtttaaa gtgaaaatgc gaggcttatg cactaagttc    2880
tctgtgacaa caccctggaa gctcgccgtt tcgattgcct tgatcgcctg gtcctcggcc    2940
catgagaaat atttaaccgc aaggttgaat acagtctcag gcgtcattgg gtgacgatgg    3000
ttcaggttgg caatgtcgcc atacttttta ttgtatagct ctttgaagtt accgattcga    3060
accttctcgt ttgcgtgact ggtgaagttt cgtctttca tagttgtttc cccttgttga    3120
ataggaatga attataccag attgcaggca taaaaaaagc accccgaagg atgcttaaat    3180
taatcaatca acgtatttga tggccccagg cttccgcccc gatcgaatat cgcaaagctc    3240
attagcaaca accatgaact tgccggatac gcgccattgc ttttcttct catcatatcg    3300 cgcttgagcg aattgtccgc gcttgattag cttagtaacc catgcgcagg aaagcgaaat    3360
gatcaggacg gaagcgaaaa taaaaccata aataaacgtc agcatgaaat accccttaca    3420
taattaacta aaaatttatg agtcgttgta tcgactccgc tcatttcctt cacctttgaa    3480
acggcttctt cggcgctact ggcctcaacc tttgcttcaa agctttgctt acaagatgcg    3540
catgtgcgcc ccattagcaa aatagttagc ttgacctcaa acatatcaaa cctcattgtt    3600
aggtccggtt acggagtccg gcaggctttc acaatgcctc gatttttttg cgacttacac    3660
tttgcttttg gcgatgcgct atttcaattt gcggcttacg aaccgctcgt tgccacttgg    3720
tggcctcgtc tgtttacgag attaaagata ccagtcagtg agatggctgt caatcaactt    3780
ttttaaaagt tccatacgtc gggcaaacag ggtagtcgat cgctaccttg ttcccctcgt    3840
cactgtagac gtaaacgaat ccctgggaat caacttttc cactgtgtac tcgcagccag    3900
taaagaactc ataaccgcgc gcgccgatac acttgatcac gtcacccttc ttgatcttac    3960
tcatagatac tttctccgtt ttcacgtttg ccaaccagac ccttaagata accagcaatc    4020
cacacaaatt tgtcacgcga tataatggtc gctacggcat catggtgctt ggtaataatt    4080
gatgcgacca gctatcatc tttgcgatct ttcttgctca gatcggcata cgctgcgttt    4140
aattgcttgg cctttgcctt tactgcgttc atttgcggat cagttaatcc aaacattatt    4200
tgtacacccc atcaatgatt tgctgatct tgttcattgt gtcaaccttg gcgcaatccc    4260
attccggtga gcctggttct tcccatggtc cgccagggcc gtgacacgtc atgttgtcga    4320
taagttccga cacttcgctt tccagcacat tgcgcatgtg ctcaatctgc cagcattcaa    4380
```

-continued

```
cagagtcttc cgcgtcgcgg taagccttga actcaccgcc gagaactttt tgagcagctt      4440
cggctgattc cttcgtttcg tgaacggtcc ggtgaatctc tttaccgaac ttgccgaccc      4500
cgtatgtgtg aatgtaaatc atttctcgat caccttatat tcattttcgc taatgctgat      4560
ttcgttgcca acatgcacga actctgtttc acggatagct tggattgaaa ggtcgccgtc      4620
cttgtattta cctgacactt cgattacgtc gccgacttta aatccgcaat cttccagagt      4680
aagggcatcg tcatctgtca catagttaac gtcgataatt tcaattttca tttctgcttc      4740
ctcgttcgtt tcgatggggt aactatacag ccaccccgat tctgagtttt aacaaaaagt      4800
gctatcgctg gtgattgcgt gcattctttt tcattgccgc gaaggcgata aagcagaaca      4860
tcccaggctc agtgaatcgt aacttgccat actggcgaca catacggcgg aatttacgct      4920
tgtcattgaa cacgttagtt acacgttttt ccgtcactac taatcggcgc ggacccttta      4980
ctaccacgaa agtgactgct gggccgcttg cgagattcag gttaaactta ctgcctttct      5040
ggatggcgta ccaggtaagg ccgttatcga catcaataac atcagccacg ttgaggtgac      5100
gatttggcct gcgtttagct tcgtacacat gaccaacctg aaagtgatct tcgaacagcg      5160
gcgctaaccc tggatgtatt ttaacgcaac gtaatttcat ggttattccc cttcgttttc      5220
gtcgaattgt tgattattga tctgagtgcg aacctctttg accatctcag agaactcatc      5280
ggctgtgcac ttcatagtct gagtagccag cagttgctta aggatggtgg cttgcttgtc      5340
tgacaggttg atagtaatca tcttgttttc ctctcgcttg gtgtgaacta actataacaa      5400
aacccgccgg agcgggttta gcaattcgtg ctatttacca gggaatatca tcggcccaat      5460
catcatccat tgaaggacta accaagcaag cgcgaactac tttaaggacg ccatcatcaa      5520
catcaccatt taccagatgc acatcatgct cgttatattt cttgtaatca gggaagtgcg      5580
attccttgat gcggatgtaa tcacggctat ctcccgcgaa agtctttcca tccatgaaca      5640
agcggaccag ggtaacatcg tgaccatctt caactagtcg aatcacttca tcggggaatc      5700
cgccatcagt gcaaacaaag cagaggcctt catcacacag cttgatatgt tcgctcatca      5760
gtttgccgaa ctgctggttg ccaaaaagcg gcttgaccac tgtttcgcta atccagatca      5820
tgaactcacg gcaggtcttg ccaccgagaa agctctgagg ctgttctttc tgatcgcggt      5880
cgtcgtatgc tgtgatgaac tttgaaaaag ccctggcccc aaggatggat gctgcaatct      5940
caaacatcgg gcgtttgaag ctggtaggga tgcagttgta atctgctgca agcgcgttgc      6000
cgatcgtgtc cttacccaca ccagccggac catttagaat gataattttt gacattttga      6060
tattcctgag tagtgggcgc gatgtgcgcc cgttaaggtt ttattattta ccgcttacga      6120
gattgcattt cgtgcactgg cgaactccat gtggaggtag cggatcgcta aattcgtgct      6180
cgcaaacttt ttctacgccg tgagacttaa tgccggagtg cacgttatcg ccatagtcac      6240
acacctgata ggtagtgatg ccgaggcttc ggaagtgcgc gataacgcta ggactatcat      6300
caaaggccgc agtgatgcgg tgcaatccaa tgtagcgcaa aaattcttcc ttgataatcg      6360
tatccttgcg gttgtcgtca gcctggcgca taaccatgac gttgtattta gcgccagcat      6420
catacagcca ttgcgttgat tcctcaacca ctgcatcaga tcgaccagtg agaacgatga      6480
tgaaagcgcc ggaagcgaac aggctattca ttacgtcaat cgtttcctgg aatggctgat      6540
cgaacttgct caatgagtta aattcaagcc atgactcagt gatgtgcaag tcctttgtcg      6600
gtagcttgtg caggcggtgc gaaccgtccg acagagtacc atcgaaatca aatatgtaaa      6660 cttcttgtt tactgcttcc gtttgaaggt gatgcttaat cattgtgtaa agctggttca      6720
tttttaactt cctttcgtgt ggttgatgtg gggattacac cagtcaggat gaatcccctt      6780
```

```
ttaacaaaac gtgctatttg atatagaact gagccactaa gctgccatca ggatttatga    6840
ttgcgtatgc atcgccaaga tcttttccat caatgttagc ctttccaaac ttaacagcat    6900
cccagcggta atcaccttt aaatcatgga agaatgcatc ttgtgcgata tggataaagc     6960
gcggctcaca accttgcttg cattcatcaa cttcatactc gtactcgcac ccgttgataa    7020
acatattgcc gttaacatga tggcaaactg ccaccttgcg atcgcgtgct gattcacatt    7080
cacccgtcgc ccatgcgtga cgatcgctat aaccgtaacc gccgcttcgt ggttccattt    7140
tcgcggttga catggtaagc gccttgcctt caccgaaatt gctaccgaaa gtgaacttgg    7200
catctttcgt caggtaatca aactttgcgc catcatctac gacggttttc cctgggccag    7260
ccgcaagctc attcacgaat gcatcgacag tgctgtgaca cggatcgcca ttgtacttag    7320
gcaaatcctt gagcaattgc tcacatgctt cgtgcaccag cttacctaca gcttctttga    7380
ttgcctgctc aacatggtca gcgataatcg acggtgcaga aatttgatgt ttttgagtcg    7440
attctaaggc ctttaaacgt gcctgtaatg actcgatttc ttttttatgc attgcgtagg    7500
atacccatgc tccatcgtcg caggattgca ttccgacgca gtgaatattg acgctggttg    7560
gcactgacac agggatataa cggttgatgc tgttcatatg tgattcctca gttggtttgt    7620
gttcacttga caggagacac tatagctaat gtctccgaga aagttttaac aaaaagtgct    7680
attggataaa tccgtactta accgcgttgg cgagggtaac atactgctta gccgtcagcg    7740
ttgagtgata ggtgattagt ccagccttaa ttgcttttac caactgttcc tgtgtgacgc    7800
gtgagatttt aacaacccca aaatcgccac cagtacgcag acaacatcg ccgaccgcac     7860 aaaactcaac ggctttactg ttagtgtaga cctgcatgat tattgctcct tcaactttg     7920 gtagatgcct ttaactatcc cgaatgaaat agccaggggc cagatagcgg caacgattac    7980
catgtcgtac cacttgttat caatattgct aacgtctttt gcaattgcat aaaccggaag    8040
tgcgcccagg atgtaaagca cgatgcataa aataatcata agtaaccctt ccctacagtt    8100
tcgccaactt cgcgtgatgc ctttaatttg ttccagaaat cgaacggccc tactggctcc    8160
catgatttcg gtttgccttc ttcgttccac caaccaagaa cagccgcact accgtaacat    8220
gagttcattg gacgcccatc gctgaaatag ctcttgaata cgcgatccag ctcatcaccg    8280
ctaaccttga ttgatctatc ctcaaattca gtaccatcaa agaaaccttc cacaacgatc    8340
gggtaagaac caggatcgcg tgggttagtc tcttttgggt ggagcttgaa gtattcaagt    8400
tcggcataga tgctagggtt aagtaaacgt actttcattt catgtgatcc gatttaagtg    8460
ttgctggtgt tacgccgtaa tgctcgatta agtgccacat cgatcgcag gtcttgcggc     8520 ctaccgcttc gatgaacttt ggcatctcaa gacggctgtt tatgcgatcc atctggtccg    8580
cgctgcctga catattgacc aggcggaaaa actgctcaaa ctcttttca gtaaacatct     8640 gcaattcctc tgattggttg ttttgcttca ataaggccac tctatcaaat ggccttgcgg    8700
aaggtttaac aaaaagtgct attcgaattt ttcgttgtgg tgaatgacct catccacgta    8760
aatctttctc aagaaccact cctgcgttcc agtggaagta atcttgtgca tcttccatac    8820
ctggtgccat ggcagatact caatatcctc agccagtgcc gtgaacgctt tgccgcagtg    8880
agtgtaaatc gtggtgtagt tagtcatttc gtatctcct tgttggtatg aaagaagtat     8940
accagtcagg gagaatatcg ttttagcaat tcgtgctatt ccacaacaac caggaagatt    9000
atcaccagga acagaagcac ccaggataat tcaacacaca gcaattgcag cacgtcaact    9060
aatttgaact tcataacacc tccacctcat cctcgctaaa tggccagtcg cctggtgcca    9120
```

```
ttcctttctt gctgagcgcc ggaaggaagt cagtgtcaac catgtacagc gtccccgcat    9180
cgctttcgta tttccaggcc atagccacga ctggcagctt gcttttatcg acaccgagat    9240
aaggtgactt gatgatgcgg atcttaatca tttcttcatt gttcataaaa ccccattctc    9300
agctcggtga gctgcttcca tcagatacgc tgctaactgg cgagcctggt ctggcgtgta    9360
caacatgaaa atgttcggat cgcagtagtc gttaggattg aagttcaagg acaccttgaa    9420
tctgtaaccc ttctcggttg tgtcgtcctg aatcctcaca gcctcaatct cggcctgctc    9480
gttgtagtca tctgcgatgc gtaccttggt actcataatt tacccattgg ttgattgttt    9540
cacttcaatg agtgcactat agcaaatgca ctcacggaag ttttaacaaa aagtgctatc    9600
gttcatctta tctggagcat cccttgccgc aaccatggcg accaacttcc acgatcccga    9660
caccgcttaa gccgatgtat tcctgaccag tgtccttatc ggtgatgacg tatatcgctc    9720
tgacgttctc atatgcaagt tcatccctga actcctgaat cttcacaacc tggacgcgat    9780
cgttgacatt cactggcatc ttctgccgag cctctgaatc tacacgggtg cttccgaaat    9840
cacatccagc cagagccagt gctgctaata aaattagttt cttcattcga taatcctcac    9900
tactttctct ttgcgatgcg gtgcgccgga cttatgcagc cagtagcgag cctgggaaag    9960
ctggcttgta tgggccactg taacccacca gaacaaagcc accgtttttt ggacggcata    10020
ccacttgacc ggatgaccga aggcagtggt cgtgtcaatc aatacgatcc tgaatttact    10080
tatcaccttc ttctgcctcc acttcctcag ccgccaggat taatgccgcc gccagcttgc    10140
gtgcttgctc tggtgtgtaa tgagccatag tggagctata ccacggtct tcggtgtcag    10200
tgtcaatgct cacgatgccg tcgtaatata cggatgttga cactcagtg ctgtcacctg    10260
caaaatcttc gataattaca gctttcatct tcatttcctc tttgttgttg atgaggtaat    10320
catagctgac tacccgattt attgtttagc aattcgtgct atttcgaacg atttcgaatt    10380
tagccattat gacgccaagg cttttttatca taagagcttc acctatcgtc ttcactatgt    10440
actcattgcc atcaaccttg atgtagtatg agccattaaa gcgagggatt ggctttgccg    10500
agtatatccc accatttaca actgaaaggt tgtggtgatt agcttgcctt acatacacgc    10560
attttataag cattaatatt caccattcag gatagatttc gctttccggt agaactggat    10620
ggccttctcc acctcatcgg catcatagcc atgaatcaga tctgagttga gctgcgcttt    10680
gctctgatat tttcgctcaa ccgcgctcca tgcgtcgcaa aaattatgga tgtctcgctt    10740
atccatccca accaggaatg ggtgtgcata atcttatca cctattaggc aagcaattcc    10800
ggcgccctgt agtgatggta ggatgttgtc aatcaggtca ttcatgactc cattgcgccc    10860
gacgaacggc tggacctttc tgattgcctc atatgttgag cgaactccca caacgccttt    10920
tccatttatc gcttgattcc agatcttttc aaccacgacg cattgttcac gacttaggtt    10980
tgcgcgacgc atgacttcta cttcgcacca gtacttttgt gactgtcggt atccgttagc    11040
attgattgca actcgtagtg gtggaagccc atcttccgta gcaatcttca taatctgctc    11100
atctgtcagc ttatcttcgt taaaatcaaa catccccatt atttcgtctc cctaatcatt    11160
tcctggtaca ttttgattgc cttgatggct cctgtaatct catcgccctc aaagttagtc    11220
acggatggca tcagcttgag tattttgacc ttaaagtcgc tcacggcctt ctctgcaatc    11280
tggccgtttg ccttcactcg ctttcctgtc tggattgcgc catcaaccaa agacagataa    11340
gcacaccgca cctcgacgtc atcaccgaaa tcaccatcct taattgaaag ttttgcacga    11400
acgtttgccg cctgcatctc tggcatcctg gctaccgtat tggcgacata tgacgccttc    11460
agctttgaca tgctgtactt gccacctaca tccagatcct cacgacttat gcctcctata    11520
```

```
tcactagatg tgaggccgta aacctggcga gctattagat ggattgggac atggaaggtt    11580
cggtcgtcgg ccttaagagc ctgctcagcc atgtagcgga taacgtcacc gaggcttact    11640
gcttctttgt gctctgacat actcattact cctgattggt tggtcttcgc taagatgatt    11700
ccatagtatc acacatctac gtgttatcaa gtgttatcgg tgcaaatttt ctgattagtt    11760
acatatttcc accaatcgcc ccagatatag ctcaatgtaa agtctgcgta tagtttgtag    11820
ataaggattt ttagtaaatt ggccccctata tgccttttta ttcctacaat gtcgtcatat    11880
tcctacaagt gtaggaagat atcatagaaa tctatcgcaa tatcacatat ccactatcta    11940
cattatctac atatatatgt attaataata ataatataga taaatggtta ttatataagg    12000
atattttaat gtaaccatgg cgtaattcat cgtgatatgc gtacatgatt cctgcggagt    12060
gctggtgtgt ctacatggca taacatgcat aacgcgtatg cgctagaaac gtgtggcggg    12120
aaaatcctac caggcgatca ggggatcaga tctcaccaca tcattccccc atcaatgaat    12180
cattgctcaa ttcgcaacaa tcgaaaacat cattgcaata gatgcaatat tgctacctgt    12240
gcaatagtga agtgaatcat tgcaatagct gcaacaatcc ataaatcgaa cgaatagcac    12300
tttttgctaa tgaccgatca ggtgtgattc gctattatta cctcatcgaa acgacacgca    12360
ctaaaggaaa tcatcatggc taagcgcatc aacaagaact caccagttac catcgaaaac    12420
attattgccc tgctggtcca ggagggttat aaccctgaga gcgccaaggc actggttgag    12480
aagatgttcg cggtagtcgt gaaggctcat ccagaagaca acatccgtga aatcgctttc    12540
tacctgaaac acatgtaagg ggtaattgat aatggctaac aaaattgttt tgaagcacaa    12600
gaacgatgtg aaggttggcg acactatcat ccatcacgga tcacttcgga ccatgggtaa    12660
ggagagcttc actaacgatc agttcatggg ccgattaatc cttggtgaca gctaccgcct    12720
tggatacgag atggtccagg tagtcgagaa agttaaattc tgaaatagca cgaattgcta    12780
aacgaagcct cacggattga ggcataatca tttcatcgaa acgaagtaca caagaggaag    12840
taaaaatgtc agttaaagtt cagaacgtag tagcacacat cgaagcaaaa ggccgtgcaa    12900
tcgtcaagct ggaccgcgcc gcaggcgtaa gccaaatcac catcacgcgc cgtgagttcg    12960
accgctacgt tgttggtaca catccaggct caatcatccg aagccttacc cgtgctgaga    13020
tggtcaatct gttaaacgat aactcacttt acatcaactc ctggagctaa cagtgcatca    13080
agataatttc tggagccgcc accgcgcggc acttgaagcc ggactcaatg aagagtgtgc    13140
gctcaaggtt gcttatggat gcatcgaact cgatgacgca ctgggcgtca tggatatgga    13200
tctgaaaagc gaaagcaacc agtcagtaga cggaatcggg gatgacttcg actaccgctt    13260
aaaatatgac gacggaatac cgttctaagg cgagatcatg aaagtaaagt gcacaaactg    13320
catcaccagc accgacaaaa aagttttaac accattcgtt aaaggctctg tatacgacgc    13380
tgaggcgcta atcattaacg gtaagacaat cccgaacgaa tgggttatta atggcgctga    13440
gcgaccgcac aagcacgatt ctggctggat tgctatcgca ggatgaaagg tcggaatgtt    13500
tatccctgga attgcaacgt ttgatgaggt gaaataatgc tcaagccatc cgatttgaac    13560
tactacgaca acgacacgat cgcgaagctc tcaggtcaag gatggtatcc atggagcacc    13620
agcgctcagg ttgaagactt gcaaagcagt tatgaaatca cacagaaagc aattgagaag    13680
gcaaagaaga aatgaataga aaaagaagtc cagacggaaa atttctggt gatccgctac    13740 tacctggagg ttttcataat tgcaactcat gcggaattaa aaaggaggct gacgataaaa    13800
actttagaac aataaataaa ggaaaaacat gcgagagcct aagcaaaact tgcagaaaat    13860
```

```
gcgagtatca aaaaggaaag gataaacacg caaggaacat gaaaaaccct gaatttgcag    13920
atgctagaag ggaaaagtgc aggaactgga ggagcaacaa cagaagtaag gtggcgctta    13980
aaaattatca agcaatagat aaaaagaaag gacttacatg caccatgaca attgatgatg    14040
ttgatgagtt gcagtcaatg ccatgctact attgcggaga tacggagcgg gttggtgctg    14100
acaggattga caactcactt gctcacacgc gcaaaaactg ccttccatgt tgccctgatt    14160
gtaatatctg taggagtaac acttttttcag ttgatgagat gatggtgata ggcaaagcga    14220
taagactcgt aaagaaatca agaaatagca ctaattgcta aagcccttcg gggcttttcc    14280
tgtatattca tctcatcgaa acgaaacacg caaggaaat caaaatgaca gcaacaacta    14340
aaaacttcgt tagcaacgaa aacgtattat acaaagctcg tgttaaagac ggtgtagagc    14400
aaatcaagaa agatggtaaa tgggttaacc tggaagaaag cggtaagtat atcaagacaa    14460
aaactcttta ctgcacgaag gttaatcaca ggtcagcagt taaaaaagac ttcaagaag    14520 gtaagcgcta tcaggtaaat attcatgctg gccttggcca atctgccggt tacatttacg    14580
atgaggatgg taatgcttgg cagctttacc gaaacgaaga ggttggcttc atgagcctat    14640
gcggtacgta caagtggcag gcggcgtaca aataagtagc attttctggc aagcggtttt    14700
accataggtg cgttaacatt agcgcaccaa ctaaggagtt ttttaatgtt tgattttaac    14760
gaagataaat tgtccatcga tcaggtaatg gctgtagccg ctgccgacaa tctgccgcct    14820
ttgcgcgttg ccatcaatgc taacgggtac aggcaaagcc agtcgttctg gaaagcacca    14880
acagaaatcg actcaggcgg tgacaaatat ccggttatct cacttggtaa cgattatgat    14940
gtcgttggta agctgtcaag caatgccgct cgttcagttc agttccccga gtcgtccgct    15000
tacatgcatt tcctcggatg catatcagcc gccatgctgg gccgatttac ggttgagtat    15060 cacgaacac aacagccgac cgctctttac gtcgtaacca gtcagccgcc atcgacgggt    15120
aaatcagcca ttaactcact ttcgctggcc ccgatgatcg cagagactga acgactaaac    15180
gagatccgaa agcgcgaccg caagaagatt atggctaagc tctccgctct atccaaggag    15240
atgaagcagg agaaatcacc atctgatatg gcggctctgt ttgaggagaa agaggagctt    15300
gaagaaaaac ttgaacgact ctgtgacatc gttttccccg tatccgacac cacgccggaa    15360
ggtcttgcgc gaatcaacaa ccgccagggc aactttgcag ttatctcgga tgaagcaacg    15420
agcgtgaact cactgttagg catgacctat ggtgacggct caagaaaaac gaacagcgag    15480
cttgtgctta aggcgtggga tgctggtaac gtatctatcg cccgtgcgaa cgcagacaat    15540
aacatgagct tcattgcgat gggctgtata tctgtaattg cacaggatga aacaatcaac    15600
gcgatcatga atgctggtgc gcgtggtatc ggtgtgtcag aacgtttctt gcttgtgcgt    15660
gagaagtcat tccttggcga gcgtgtattc gttgacgaaa aaggcgaatc aacatacgag    15720
cctattgatg gcggactcaa ggcggactac ttccgtctgg tccatgagat catgagcgaa    15780
cacgaagtca acctgacagt gagcacgtcg gcgatgaaat atctcaaccg tgcgcgtcag    15840
gatatggaac tccaccttgc ggacggcggg aagtattcac acacaatgct tcgcggcgcg    15900
ctgggtaagt ttgataagca ggccatcagg atcgcggcgg ttcttcacac tgtgcgtaac    15960
tggttcaatc ccaatggcgg aagtccgcag aagtcaaggg agattgagct tgacaccatg    16020
caagaagctg taatcatgtt ccaggaactc agtaaaactt atctgtcatc tgccaatgct    16080
gctggtcacg ctggcgacca tgcggagatg aacaagctga ttgacatcct gatcaagcag    16140
ggcaagaacg ggaagggcgt tgtaggtgtc agatccctat atgaagcggc tcgtaaggtt    16200
aagccttttg aggggcaaag tggtgtgatg actcgcatca aagaccacct aatccctatg    16260
```

```
ctggatgaga aaaactatac gtgcctgatt ggtgataaaa tttacattaa tccgagattg   16320
ctggggtaaa caatgttcct gctcgacgtg taccggtttt gtgaaggata tgaaaagttc   16380
aatcgtcagc acctggcggt gttcatatac aagcacaggg agtgtgagcg actggcgaag   16440
gctgccggag ttacgcctcg ctacttcgca tcatcagcat caaaggagtt catcgcaaga   16500
tgcatgggcg aaggatacct tgacggcgtg aacaactggt actggtccaa aggggcgcaa   16560
aaaaggccgt ttgaatttca tttcaggtgc tatggcggtg agaatgatcg ctatacatgg   16620
gagatgatga acatagagaa tatgagcgat aatgagttat tcggaaagcc aggtcgtaat   16680
cgacgcgata atcagatgca gttctgagaa tggcatcagt gaggatgggc ttaaccaagc   16740
ccttctttca atgcttaact catccatgcg cgccggacga cgtgatgagc atactctatg   16800
caataatgaa ggtgaattat tgcttctggt gcaaagattt ggataaaaaa agggagcctt   16860
tcggctcctt ttatttttg cgtcgttcca gccatagata gaaaattacc atcagaatac   16920
cgatgaacag gaataccagc ccagcaatca gattaccttt tgagtcattc ctgatctcaa   16980
tcttatcagc gataatggtg tcagctttga tgcttgatgt gctgacagac ttaccgtttg   17040
acgtatcaac cttgccaacc ttggaatcct taatcgtggt gtcgttgtag tttgacttat   17100
ccacctttcc ggtaacgcct accgtttgct tcacgttttc tgccccagcc tgcgcgctga   17160
tttctggctt actgccaatt aaaccagtca gggcagatgt tgctgaacac cccgttagca   17220
taattacaga gcataatagc attttttgca aaaacataaa ttaccaccct tgatatgatt   17280
gaagtgaaaa ctacatagga gattatacat gaattggtca gattacttca catatgatgg   17340
cttaaatctt tggagaaaaa ggaacgagag caggagtgcg aattacaact caaggaatga   17400
gggattactt tgcggcacga gcgacaaaag aggttacttg cttgttagtc tggatggtaa   17460
aagatacaag gcccataggg tggtatggga aatgcacaac ggaccaatac ctgaaggtat   17520
ggagatagac cacataaacc atgtgaagta tgataacagg attgataacc taaggctggc   17580
gtctagatca gatcaatcta tgaatatgcc aaagtcagta gcaaacaagt caggagttgt   17640
tggtgtctgt tttaataagg ccagaggtaa gtggttctca cagataaaat tcaatggtgt   17700
aaacgagaag ctgtactatg gagactcttt cgaggatgct gtaaaggcaa gaaaagaagc   17760
tgagataaga ctcggttttc acgagaatca cgggggcctaa aggccccttt tcatttccat   17820
ctcaccttca atacatagct taatctcaat attcctcctg tttaccagtc ccttaacgac   17880
aatcttcttt ccattctttg ttattttatt ccacataccc aaagctttac accccttgat   17940
aacctcacct cgattaatta acctgatggc tgtggagtta cgcatggcac taccgccgac   18000
attgtaacta aaactaataa gagcagcttt tgtcttgctg tgtatatcgt acctcaccgc   18060
ctgctcaaca tacttactat gaattgctac atgttttca gtagagccc tacactctga   18120 tttgctatat gttttcccaa taactacgtc tggcccggta ataccactgc aaattgtcca   18180 cacccagca atgtcaatgt aaggtctgtt ctccacaccc tcaacaagct caataagcgg   18240
cgctgcgatg tatattgccg cagctgtcgc cgcactaatt aacagcttct gcttcattta   18300
cttgctcctt atcttgattg ctgtttttaa gtctcctgac tcaagagctc gccgaatcgc   18360
ctggctatcc ttaaacttcc agtaagcccc ccaagcccca aaattatta gagcgataag   18420 gctgattatt gctatagtca tttggccagt tgcggctcca gtaaccgcag cacctccggt   18480
tgatgccgta gcggcgttaa ttacttccct catgcgatcc accttatgt atttgtcaat   18540 gtttaagtta gtaaaaacat aatacattag aacggtatga aaagaagca caaaaaaagg   18600
```

-continued

```
gagcctaaag gctccccgtg cgtaacgtta tgtttttatt gcgctagtca gcgataataa    18660
attcaaccag cgcaccatca agcggagcaa aaatccatgt catatcgtcg ccgtaaatct    18720
tgtagttact gtcgccctgg tattcggcgc tgtacggatt gttaacagtg aaaggcaggg    18780
ttttagatgt gttcttaacg caaaataatt taaccatgat tgaaatcctc tgtgagtgag    18840
atatgaatat agcgccatat aggcgctatg ttttaacaaa aagtgctatt tacataccag    18900
ggcgataaat gtgtcgacca acctctccga actccttgtg gtaaacaatt gcagccgctt    18960
ggcggtatga tcgccaccct ccgcgagcgg catatgcatc cttgctagcc agcgctggat    19020
gaacctcgtc aatcccaaga gtgcactctg taacagttgc atgatggaaa tggccggagt    19080
ggcagtaaac aaactcacat tcaccaaagt ctttgcggta gtcggtcgcc attgctgcga    19140
gtcgaccctc agcttttcttc atcgtgtgac cgtgcgtgta accaagtagt gttgaaccaa    19200
atcttgtttt gtgcatgatt gccggactgg tatcaacaaa cactcgactc tcgtcttcat    19260
aaaatgcagc cattgccgcg cgaagccaaa tcataccact ttggtcatga tttccctcta    19320
taatctgaat ctcgacattt ttatgctttt taagcatctt ctctactgca ccacgaattg    19380
agcgaatcgc aacataaact aacttagcat atcggctatc ctgatcaagg cagtgtccgc    19440
ttgctggagt taccgcctcc aacccatcag agtggaggaa gtctccacca actaaaatca    19500
cggcttctc tgaggctggt gatacagaga ttgcgtggtc aaaatatgac cccattaatt    19560
tctctgccgt tttagtgtca taattctcac cagattcatg gcgatgtgcc atcatgccga    19620
tatggatatc gaaaataggg taaagagtca ttaattcaga cttgacctca ttgcctgagt    19680
ggattaccac atctgccttc ggcaactccg aacaaaaagc ctcacgcgcc tgttccatca    19740
gaacctcaag gcgctcatta tcaattgagg tcttaaccca ccggatcttc tcgttacctt    19800
ccgcatcaat catggttgac gtgccttttta cagcgaatcc atcaggaaca tatttagcaa    19860
cagctttgtt accgtgtccg tgacctttct tggccaggtt gcttgagcgt tgctcaacag    19920
ttctaatgtt catcccatat tcctgggcga tctgacgcag tgttttacca gcttcgcgct    19980
cggcaatgaa ttgttcgtca ctgattttt gaatagccat ttttgtaaat ccttatcgtg    20040
ttagcaagta gatgataata aaaccaatta tcggcggtaa taatacagga attaggcagc    20100
gcatcaaatc tttttcaacc atgttgttaa agtatatggc tcaaccgctt cacctgccgt    20160
ctctgattcg ctggggacca tcataccagt tgacgggcta aaatacatca ggcgatagcc    20220
gccaccgcgc gaacatggca catcttcgaa gtcagaaggc aaccagtcag caaaagggat    20280
gatcgcgaac gtctcattgt tgttgctgca ggtcggatat ttgtcagcgt caaaatcaag    20340
tcctggtaag ttcatttata tcttctcgct gcgtctttcg ttgcttgaat gaaggctttg    20400
tagtcaatct tcaccggagt tgccggaact ctgatcagct tacgtggcct ttcgtgtata    20460
tacgtcattt tcccgttgaa gatgacacat atgtctttaa tatctaagta cttagctata    20520
agcgcaatgt catcacttat tcctgcttcc ttgcagtgat tccaaacagc ctgacggcct    20580
acatcaacag ttaccataaa tatcaaagct ccccgacatg gcctgataat ctgcgatagg    20640
caaatgacca taagcgcccct tgagataagt aacagcaata acctcatcca gtccgccatc    20700
cttgccaagc gccagcgctt cacttgcgca atcattagcc aggcgaagca ggtgcggcag    20760
taaaatattt ttacggtatg cttgctggtt gtaagtgcta aaaggttgct tcttcatggt    20820
gattcctcgt ctcgttggta tgaaagaagt atcccgctc ggcggcgggt atgtttagca    20880
attagtgcta ttgtgcgaaa tcttcggggc actcgcgctt atagtcttcc atatcttttc    20940
gtattgcagc gcgccatgat gatactgact gatctttcaa ctcatcaaat gacatatcaa    21000
```

```
gatcacctga gaataaccac gcatcacctt tgaaccctga acttgttaac tcatcgcaaa   21060
cgatcgcacg aaataaatga aattgatcat tgtcggttaa attgattttt acactactca   21120
tcttaaacac tcccgtgatt tgtatagtta ccacaaacta aatttctcat ttcaactatt   21180
gccaaccttg cctttcaat atcatgaaag tagccagcaa gataaacaac accaccaacc    21240
gtaaccatag ccctccagca attcattggc ttgcaccagc ttacacccct gaccccagat   21300
ttgttatttg atttcatagg catattttgc tgattctgac ttctcgttac aagcttagg    21360 ttttcaatcc tattgttacg cttgtcatta tcaatgtgat ctatctcacc tttaaattca   21420
ccataaacaa attcatacgc aagcctatga gcaaggtgct tcctcctacc aacagatact   21480
gttatatacc cacgattatg atctgtactt gaaatcctgt tgaatctcaa gttaatgaaa   21540
gcgccagtat cagtatcgta gccaattcct gggtacttac cattctttat tatcactaaa   21600
cgctcctttt ccttgctttt cttgatttaa ttgatggaca aatctcagtc gatgaaacat   21660
atgtcgtttt ttgaacctcg ccaacaccta gctttctcat tataaatatt acagaaccct   21720
tattattacc agttacaggc tttccggtca gtccagagat gaatgccaac cgccccgtcc   21780
ggcaatattc ctgactgtca atctctgtga tgtcagcctc aatccagatg atttcagccg   21840
cgttgcgacg ggcctcggca aaccatgccg tagagttatc accaggaagc aacatatcaa   21900
tctgattgtt gtgctccatt tgctcaatcg ctttcttcac gaaaggatct ggatgcgagt   21960
acggcggatt aagccagatg tgcttattgc tacccaccaa gatcttaagg cagttcacat   22020
gctcactata gaacttttcg caaactgcat tgttagcact tgcggcggcg tcgatgtcat   22080
atttgccata acgcgattcc atccatgaaa tcagctccct gtctgtagcc caaagatctc   22140
gaactgcgtc aggagtcttg cttccggcat atctgtttcc agttaccta tagaaggtgt     22200 ccggcttaac cgactgataa tgaccgttac caggaacaag ctcattggta acaaagtttt   22260
cacgctcgat ctgctcaaag ctaacgaatg cgtcatgagt atctttgtcg cttgagtcga   22320
tcatcttatt taacctcggt aactttgcag ttattcacag cgacgaaccc gccgacgcta   22380
actttgacct gactttcagt cacgttgtaa attgcctttc ctaagaaagt ttgcagctcg   22440
tagtgatcgc cttcacgctc aattacaaca cccttgtctg aaacaatctg tgacttggtt   22500
actgtgaagg attcattgcc gcaatcgtaa aacttggtat cttctgcaca acctgccatt   22560
gccacaactg ccagtagagc gatgattgac tttttcattt tgatttcctt ggttggttac   22620
ttcgtatcga tgaggtgata atacaccacc tcacggattc gtctttagca attcgtgcta   22680
ttcagcatat ctgcaacggc tttcttatat tcctcctggc cgtatgccac cgccgcgaac   22740
ccgccacgct cccggacacg ccggaggaac tctttctgct ccttgctgac tggtgatgct   22800 ttgccttttcc cgctttatt gactcgcttc aattctatgg ccccgaaagg atatttgccg    22860
aacagaccta gaaggaatac gaagtcacta ccccccttca ataatccact ctgagcatcc   22920
tttaatgctg tatggatgtg cttccttgttc tcattaacgg cgtgccagaa cagcaaatca   22980
ccatgcctaa ccttcgtcca agtcacacaa tctacttggt gcttactttc cgtccatgtg   23040
tcagatttgt ctggtgtgta atattccagg tagtcgcctt tatctttat agccatttt     23100 gccaccgtga ttgtcgtgaa agttatattt aacgtttgcc tcagttcttg catctatagc   23160
taaatcaata tcgctaaagt aacctagcga tatcttcttg ccgtttactt gtatctgagc   23220
tttccacttt ttacttgttg agcaccagct aacgccagta aatccgctac tattcgactt   23280
tcttattgat gtatttttca tgttgtcgga tctgcttact agtcttaagt ttgaaattct   23340
```

```
attatcatcc ctttcgtgat ttatgtgatc aacctccatc ccttctggta tttcaccatt   23400
atgtatatac catatcaccc tgtgctcctt taggtgagcg ccttcgaact tgaacaccct   23460
gtagccttca cgatttacgt gacctaccct tgatccaatg ctaactctag cccttggacc   23520
tgatggtttc gtccagtata gccctccatc cttgtattca acaaagttta taatcataag   23580
ttaccttcca gtccaaaatc cttacgtgat ataatatctt cacctttgc attcttgcgg    23640
tgagttaccc tcaccggatg cgctatgtgg tgagcattgt ttaaaatcat tttcgcactc   23700
ctgtaagccg ccattaattt tgcgacctta ctgtcatgca catgaggcaa tacccctttt   23760
tgtttccata tcgtgtgaca tacctgtgcc gttgactgag ggaaaaactt ctcatacgcg   23820
atgaagttaa ctcccactga gtccgtcagg tcgtaccgat aaagaatgcc agtctgatta   23880
cgcgtcagcg ttacttcaaa gctgttaact gtgcaccagt cgttcttggt gtaagcctta   23940
ccagtcagat tatcattggg atctttcaaa ctaacgtcac agcagcggca tattctcgct   24000
actacgtcat tctcagtgcc acatccctta gcaataactt cgccagtgcg atcatcaatc   24060
tggtcttcgc atatacgaga tttccagaaa tactcacaac gatttccgtt ttcgtctctg   24120
tgaatgcagc ggcgagcgta aaagctgttc tcggttccgc acagctcaca tttcttaggc   24180
tccttcttgc catcaaagcg cgctggtac tgtgattctt caagtattgg gtcaaagtat    24240
aactgaccca gctcgtccat gcaacccgca aaatcccaca ccaggtgatc ttccttcacc   24300
attcccatct cttttttgcca cggcttaagc aatctctac ctcgaccaag caactggatc    24360
agcagagtaa gtgaaccgat tttgcgaagg attaccgaaa aatcccaaaa cggaacgtta   24420
acgccagtgg ttagcgccat cacctggaat atgtatttaa tctctccacg gttagcggcc   24480
tccagtatcg cttgtcgctt tttagtattc gtcttctccg tgatgatctc ataggtagcg   24540
tcaggtggca gatagcttgc cgcctcctta caatgtcgct gacctgcgca cgtaatcagt   24600
actccgtttc gtttcttagc ttcctctacg accatcccca tgattcgctt ggtcatgctg   24660
gcgttgtcat ggattttctt ctccatcgcc ttcatttctt tctgactgaa gtcagacgtt   24720
ccatcctgac tggacgcctt aaactcatcc agatcatatc cagcgtcacc gacacttccg   24780
aaaatggttg ggacaacaga gccgaactca atcaggtagc tggtgtcgat gttagtaacc   24840
tgctcgcgcc agaatccagg tagcttaggg ttatcaacaa cgatcggggc cgttcctctg   24900
aactcggaac cagtcatgcc gaagatgcgt aattccttcc cgttcttctc tttgcagcgg   24960
cgcatcaatt cagtgataat gatcgtgtac tggcttcgtt tggttccaag aacaggctcg   25020
ccagtcttcc ggcttatcag caattgctta tccatcacct gaacgccaac ctctacgcca   25080
tcaaggtatc cattgatata gccttcgctg ttttctcgggt agtcaacgaa tacacgctca   25140
tccttttcag tgagcatcat ttcaatcgtc tcttcgttgt cgatagcggc ggcaaggtct   25200
tcccaatcca cctggtgaca ctcatcaatc ccaagcacca tgggtgtaaa gtcaccaagc   25260
gcctaaaaca gaccatttgc aacagaacct tccgaaccta caacgatagg aaagtaagct   25320
gatttcgtgt tcaggccagc gcaataaact gagttaggaa cgccgaagtt tgagatctct   25380
tcactatcct gagcaacaat gtcgccctgg cgtgcaagaa tcatcatcga caatcccatc   25440
tctttgacgc gcgatgcgat catggcaaag ccgattgttt tacctgccga caccgacgcc   25500
ttaacgatga atggatgctt atagcgagca atgcgctttc cgatctcgtc atacattacg   25560
cactgatatt cataaggaac catgtcaccg aacgtgaatt tatcctgaat ctctttaatt   25620
ttctgcgggc cgagttcttc tatctgtttt ttaatggatt taatgcgcat agccatagta   25680
ttaaatgcct ttcatgttcg ttcgattgac gttataataa caaccatcga aaccaatgtt   25740
```

```
taacaaaaag tgctattgag gtgataaaat gaatgcaact gataagcgta ctcttaacgg   25800
taacaacgga actatccgca cagaagataa gaagcagcgt aagcgaccgt caggttacta   25860
tgttctcaag gatgaagtaa aggccggatt aagagcgcga cttgatattg tatttgagtt   25920
ctacggcagc aaggcgaaca tggctaagca attaaaggtt actcgacagg ccgttgaaga   25980
atggtttaag cgtggaatga tgtcggcgcg cggcgctcaa ctggcgcaca accgatataa   26040
gcgaactggc gaaggcttcc gcgctacatt ctgccgacca gatttgcagt ttgacggcaa   26100
cgggaagccg cttactctgc ggtgcaaaaa gcgtcacatg ctgcgcgtgg tcactgaggc   26160
tgaactagca acaaagccag agtgtcgatc gtggcgaaaa attaaagcag caaacgaagc   26220
agcacgaaaa gctaaagaat gacaatcaag gttgtgccat aattggtgca accttttta   26280 ttggagtaaa tacagtgaac gacgaaatga tgtaccaaaa agaagaagtg ctgccataca   26340
tgaagggact ttggaaggag gcgctacagt caatctgtgg tcttaatgac tcatacttta   26400
gtaagcgcca tgggccatgc ccgcactgcg ctggaaaaga ccgctttcgt tggactgaca   26460
atatcaacca ccctggtgac ggtggtgccg tatgcaacca gtgcggtaac gactctggct   26520
gcggatggat gatgaagctg actggtgagc cttacagtga ggttattaac attctcggtc   26580
gattccttgg taaagtgcca caggattaca aggctaaggc ttaccgcagg gcgtcgcgcg   26640
taccggaaaa aggacttggc aagatggcag atcatgagtc gtgcgttgct gtaatggagc   26700
gcacggagaa acgcgatagc accgatttaa gtgtgtatga gtgcctaacc gaagattcgt   26760
atgatgttgg cgtaaaagtg cgtcagaatg gcactgagga gctaatacac gcactgccgt   26820
gctacatggt ccaccctgac ggaattgatg aggatatgtg taacgtcatg tttgcttatg   26880
ataatgcgca atacactttc cttgcgcgtg attattctcg cggttcagtg gttaagctag   26940
ggagtggcga ggatgatgcg gcaatatata tggcaagcga ccttattgat ggttatcgcg   27000
tgaagatggc aaccagtcag gaagtgtggg tgactttctc ccctgagaat cttgagattg   27060
ttgcttatcg gtatcgtggc gatagagagt tgagagtggc gtgtccagct gatgatttgc   27120
gaacgcttta catggctgat gagcgtgatt taaaagttgt agtgcctaac ggtggcaact   27180
tcaagatggg ccttgagcga aagctatata caccgcagga tctgatagat aagtattcat   27240
aaaaattacc cgctactgcg ggtttttta tgcctgaaag atggtatact gcatttagca   27300
aatcgtgcta tcaaattaaa ttaaggattt acaattatgg cgatctatga tgcaggaaca   27360
gcctctctag cggcagatgg tacagttact ggaattggaa ctacatggag gcagccacta   27420
acgctaatcc gtgttggtgc gactatgatt ttcaatacca cgccagcgag cattgttacc   27480
attgctgaaa ttatcagcga tacagagatt cgggttttta acgataaagg gtttactgcg   27540
ccagctggaa ctcagtactc aatacttgcc catgatggta tcacagttca aggactagct   27600
caggatgtgg ctgaaacatt gcgttactac caatcacgtg aaactgaagt tgccgcagct   27660
gttgatgctt ttaatcagtt tgatgcggat gcctttcagc aaagcgtgac taacgttaac   27720
aatcaaagcc atcaagttgc caccgatgcg gcccaggttt catctgataa ggccgacgtt   27780
tctgctgata aggccgacgt ttctgcttat aaggatgcgg cagcaggaag cgcggaaagc   27840
gcacaaaaat cagcgcgaga ggctgcatca agtgcttctt ctgtatctgg agcattagtt   27900
ggctcatttc agggtggtat tacaatccag tcaagtagtc aacagattat agatttaagg   27960
aatgggactg cgaaatctta cctttgggct ggagatttac caaagttgt accagaatca   28020 tcaactccag agtcaactgg tggtatatcc tcttctgcat ggatcccact agcatcatca   28080
```

```
tcatcagcaa ggtcagttgc tgacttgtca tcattggctg gatcgattgg tagttcagtt    28140
taccttgatt cttatattga aggccttgct gtcggtggcg gaaggttgac agctgttgat    28200
gaatcaacaa tcgttgataa cgtttcaacc tttaatggta acggtgtggt ttggaaaagg    28260
gataaaaaca ccagatcttt taccgtgtca gaagctggtt acacagatgg tttagatatt    28320 gctatttta ttaataggat taactcatct ggatttgatt gcattgtaaa tacaaacgga    28380
accgtgtttt cttctgtgga gattgacata tcaaaaggcg cactaattgg aagtggaaag    28440
tgcatcttga aggagggagc tggagctaca ggtgattact tcttaagggt attcaattct    28500
aattcagatt acacggatag agatccatta aattcaactt cattaattga ggggttgct    28560 ttcgttggac taggtgcaag gcgcattgct tttggtgggg ctggtagcgg agaagttgca    28620
gaggttttaa tatcaaggtg cggattcata tccactggag gcattgaatt tcttgataac    28680
tcttacaggt tgctatttga taagtgtaca gtatcaagaa gcttcaataa tacgttgta    28740 tttaactctc cacagaactc tggtgaagta atgaagttcc atcactgctg ggtagttgat    28800
aatggaggac cattaacatt taacaacggt caatttatat ttgattcctg ctccatgcct    28860
gccgggcaaa aggatgggta tcctcaacct actgttattt taaatgataa tgctaccaca    28920
gtattctcta acgaaacat tgagtatcaa ccaggtcaga gttttgttgg attctcagta    28980
aatggaagct caaggcttag cgtaaaagat actactgtag ttgtctatga tggattctca    29040
agtgttcctt ttgtttccaa tggtgactcg gttgtttcat tgtcaaactg ctctttacca    29100
ttgtatggag ttagcacaat agccacagga ttcccaacaa ggcagattgt tggaggagat    29160
tcaagtaaag tatctagcta cggatgttac cctaggtctg gatttatact ttcaaattgg    29220
aatctgggaa gtattgttag ccccttacata aatagcgtgg caaataactc tgcacagaac    29280
ggagtcgggt caggatggtc ttttaatacc ttaaatggaa cgccgtctgt atccgttaac    29340
aatgatgtac ctcaagcggc aatgtttggt tcatcttttg ttatcagcat tccagactca    29400
gtctcttcat cgaactttgt tcaaaatgta tatcgatgcg agcctggtag gtactttcag    29460
tttggatttt gggctaaaaa cacaaccaga acgttagctt ctataaggtt tttatcaagc    29520
ggaggtcagc aagttggcga ttcgattggc tattatatac ctcaagatgg aaagtttgat    29580
ttttatgcgg ttgtttctga tgtgccgcca ggggctgaaa gggccgagat taacttcaac    29640
tgctcagacg ttgcaggtgg acttgttatt cacaatgtaa tttatggatt aatttgataa    29700
aaaagccccg aaagggctt tatctttaac atcagaatgg aatatcatca tcgaactgat    29760
tttgctgctg cggttgctgc tgcggttgtt gctggcgttg ttgctgctga ggctgctgcc    29820
gttgttgctg ctgaccttgg ccctgctgtg ctggctcacg ctggctgaat tgcaactgag    29880
gtcggatcat ttcggcggtc acatacacag taccgtcatt tccatggcgc gacgctaagt    29940
gaagcgtgtc tgcggaaatt gatacaacct taccttcctg gaacgcttca tcataccact    30000
gcatgacgtt ttcttttgcg aagaactag cgcggtagtt gctgtaaacc gtttcatcct    30060
cgccctgctg attgcgaatc ttcatacgct ctgacagttc gacggcgtac attttccagc    30120
gaccattatt gttactgcct tctttggtga atggtgcttt gcggatctgt ccagtgatta    30180
cgtgtggcat tttatttcc ttttggatg gggccgaagc cccgttaatt agaattgctc    30240
gatggattca gattgtacag gctcggacgg tgcatttgca accttgtctt caaccttttg    30300
cgcatctgcc ttttttgctg gctggaaacc gcgagcgcta catatactca attcagcctt    30360
acgcttctgc aagtggtctt ctgcaatctt ccattccgcc gcgccaagtg aacctttcgc    30420
gctcttataa atcacttgga gatcttccag cttttcacaa ttggtgatca gttttttgta    30480
```

```
gtccgctgcc gtgcgcttcg cgatttctgc gtcgtcatcg ctctgagtga ttccaagcgc   30540
tgcgcacaat gcgtaacggc gaccgtatga agttgtcgat ccgtaagcct gggcgctaat   30600
cttctcgatc ggcatgttgt actggaacgc aagccactcg ccggaactgt gcaggatgag   30660
tgtttcaatg tgcataacct tttcggttga cgtgtctata tttgactgga taaccataag   30720
gtcatgttct ttcagtgctg gctctaccgc ctccaaaacg tccgtcaggt ttgagtagtg   30780
ggtttttagg tgagcgttat agcctgattt ttttgcgatg gcaaactgct ttttagctgc   30840
aattagagcg gatgaaacat tcgaaaactt ttctgatgta cgcattatat ataccttttgt  30900 ttgattcgtt tgatttacgg tgattatagc aaatcaccgc gttcgtgttt agcaaaaagt   30960
gctacgcttc cagaatgtgc ttgaactgct ttttaatcca atcaggagtt tcaagctcaa   31020
tctcaggttc gccgttattg tatgaaggcc atacgtcgtt ggcttcacac attgagaagg   31080
tgtgtataac gctcatatac tgcgcgcgcc caatcttaag ctgatctccg ctcatccggt   31140
acgccatcgg caagtatggt tctttcttct cctgtgccag caagcgcaca acaactggac   31200
gcgtttcttc aaagcattta cgaacaagt cacgctgcaa tgccatcttg aggtagtatc    31260
catgattgaa cgccaggcgc gggaactcag tcggattggc gctcattgtc gtcttgtaat   31320
cagtgataac gacaacctca gggtgaatct cagggtcgta tcccattcgg cggatggctt   31380
ctggatcatt aatgatgtca acgtggtcaa gtctaacctt gactttcaca ccgcaaatca   31440
cgccaaacaa cgaatactca cgaaatgctg tttcgctgtt catgcaagca ttatgctcag   31500
gaatcatctc aagaacctga cgcatactta cgcaagcatc gtagtcttcc gccttaacca   31560
gttccacgcc atcggcccac gcctgacatt gtgcgatcat atcaatcagc cacatgacgt   31620
tgaggtcttc gccgcaatca accatcatct tgatcagttc tggatattgc ttaccgcttg   31680
taccagtcag gccaaatgat tttaatttcg ttgccaatgc tgcctgacta gtgatcacgt   31740
tttcaatctc gctttctttc ggtgcgcggc gatactgacg ctcaaacagt gctttgctct   31800
caaagttggt atgcgactgc gtaccgaaga ccagtgcctt agtcgtcgag ttcatttcaa   31860
acttccaggc tgccggacaa gtgctatgga tcttactgag tgatgagcct gatacatact   31920
ctgatgtcca ctcatctttg ctgtggtaaa agtcgttgct catttcttct gacgtgaagt   31980
attgaaacag tggcttggtc atctatttaa tcctctttcg ttttttgatgt ggctaactat   32040 acgcgcttgg ttgagttagt caagtggtta cgtgtagata gttgtaatcg tgtgtatgca   32100
atggagctag ttacataaaa tgtacatacg acccagctat agctagatgt aaatagcgtg   32160
tatatcgtgt ataccacttt tcgcggatgg tgcattagtg tatgcgtgat tagatactgt   32220
atgaatatac atattagaaa tttataagcg gaatactcta tagaagtagt tacacgatat   32280
acacagtaat atatataata ataataatta tagtagaagg ttgatatata tagatatttt   32340
aatgtaacta tcgcgtaact aggcgtaact gcgcgtatat cattttccgc ggacgagatt   32400
gtatacaccg agttacagcg gttacgcgta tacaatagca cgaatagcta aagactcggg   32460
cgctagttgc atgtatagtt actacatcga aacgaaacgc acttaatgag gaattagaaa   32520
tgactaactt aatcaaactt tcaatcatcg cagcagcagc aatcatgatg gtaggttgtt   32580
cttctggtcc tcgcccagat ggttggtgtg caacgcaagc aaacggcgtg tgcgtagcaa   32640
aatggaaagg tggcgtagta gttccggctg gtgaagttga tgtgcgctac gatggaatta   32700
aggccactgg cggcggttac ggtgggtcag ttaaagacca cggaagcaag gagtggaaat   32760
aatgcctcaa ggtatcctta tagacttgaa tgacggaaga cctccgatgc agataacggc   32820
```

```
tggattaaga gcgccagctg tatctggagc gattcaggct gacgggtttg attctgctaa    32880
ctcaacatgg gacttcggat tgtcaatgac acctggttca acagcttttt gcctaccaag    32940
ccaggctgtc tatgttgatg attttgatgt tgttccagag gtctatttcc tcaatagctt    33000
ctcaaaggtt agcgattctg tggggcgtat tgggatcgga aatttcaatg gttcgaatgg    33060
tagactatta agattctacg gtagttgttt tgagatacta cctgctacag ctggaaatca    33120
ggggttgctt gtagaaaact caactaactt tgcagccata ccaaacaacg cgagattgat    33180
gagtgcggcg tatgtaggtg gcttgcaggt taatggcgca gcaagccttc cagtatctgg    33240 gataccttt ggtatgtggg ataacccaaa cgtatcattg gagtctgatg ggtcaacaat     33300
atggtgtaga gacataacat acggcggaac tgatgacgtg accgcaagca cacatgttaa    33360
tcttgttata tttaacaata caccgccacc gccaggccca ggcattacaa tgagcaatcc    33420
cgccgggcag atagtgttct caagtgtgag gaggccattt gtacttggtg ggttcattca    33480
gatcaataac aactggcaat atgtgggtgg gttcttccct atacttagat gtggagcaac    33540
aacaagagtg actggtggtt acaacaacct taggtacaaa ggtgtctgta tgtcaggtgg    33600
caatgttaga gcagctccag gtactgtaat tggtaactac tcaacgcaat caggtgctca    33660 atttccatt gatacaaaca tatcaatggc acttcctttt accccaaaca tgtattaaaa     33720
gaaaagcccc aattaagggg ctttatctat taccatactc caactacaac ccttcctccg    33780
ttcggtaggt taactgtaat tccgttattg ttaatctgaa ccgtgttatt agtgccgtta    33840
aaagcaaaat taccattgtt agcgtacaga cttccgcgaa cagttgcgtt actcaactca    33900 gcaaaccag atttatcaat agcccacccc tgacttcctt gaacgtagtt gttagattgg     33960
atcctgttac caatcttcgc gttcgtgatt gaaccgtcct tgatcacagc gctctggatg    34020
aacacctggt tgctctcaac aacaaaaggc aatgcccact gaccggaacc agaaccaata    34080
ccgttactta tagcgaatct gtttgcgtca aaaataaatt gactgcgaac attgtcacca    34140
cttccaacta actccatact catccctgcg ctatactcaa ctccattgta tttaagacct    34200
aacttaacgc cgtactgagc gccagcggat tccgcatcta cccatgagtc aagtttttca    34260
tttagtgctg cctgcgtatc gccaagctga gcgctcaaag ccgtgtcggc agtagtcctt    34320
gcttcagttt cgtttgctag tgccgtctga acttcagtta tggaggctac gacctcatca    34380
tcaatctgcg ctttaagctg cgtgagagcc tctacgcgag cctgagtttc atcagcgata    34440
aggttcaccg cctgaacata ttcagcctta cgcttgccgt tttccttggt cattcgtcgc    34500
acgtcagtat cgtttgcaag ggcgttttca agaattgatt ccgcttgcgc ctgaatagct    34560
ccgtttgact caatggcatt ctgctgtaga tacttaaacc cctcggagtt ctcgatatca    34620
accttaattt caccaatgat cgattcaacg tcatcgctgg ccattcctcg aacaatgtca    34680
gaccagtcag agacgttccc aatcctgtcc accaatctcg ctctgtacca gttcacatat    34740
cctgctggca gtgtcgagtg ccagtactcg tactgtgggt atggaatcat tgttaacaga    34800
cttgcattct cctcaccagt gtgacctcca gcaccattat ctggtatctg ctgcaactcc    34860
gtgtatgcag tatcaccaga tccttcaggg aatccccatt taaccctaat cccaaacacc    34920
tgatcgtcag atgctgttac tactgttggt ttatctggtt tcccaatctt acccgtcaat    34980
cctacactga caacgtcaga ccatggagac gcgtttccac cgcttgagat actccttacg    35040
cgtacgtgat aattacctgc ataaatccct tctacctcaa cctctgagct tgctgtacgc    35100
ggtacattca tccaattacc gttatccttg cgccactgca cgtcgtactt gcttgcgtaa    35160
ttaactttat cccaacctat caccattgtt tctacgctca tcccttgtac aatgcgcgag    35220
```

```
tatgatgaaa cgacgatgtt tttaggtggc agcatgttgt caggatcaac aatacttgtt   35280
ggtcggtcat caatatttac gccgtagtct atctcgtcgt acttattggg atcgtactca   35340
accgctgtga tactgtatgt aaactcatca tctccgtctc ccttcgtgat tccagtcaca   35400
acgtattgct gcaaagctat gtcagttcgg tcgattgcga atacagtgtt gggttgaaca   35460
tcaaagccga agccaacgtt aatctcaatc gtcttgccat ctgccgacac cttcgaaatg   35520
gtccggcgaa ccggattacc gtcaggcttg ttgacgataa tgaagtcacc agcgcgagca   35580
tcaaccttaa agtgagtgaa cacttgcagg ccagagactt ccatgacgcg acctgataat   35640
gaaagcgtca ggttacttga ccagaagtta tcagcgattg ctaccacgtc gccaatcatc   35700
gggatcatac cctcaagacc agttgcaaaa ctcaccgtcg tgctgcgaag gtttgtttta   35760
agaacccagc ggcctcgtcg gttcgcctcg cttcgtcgag tacatccgat cgcggtgatg   35820
cttgtagggt tgtgcccgaa ccgtaacgat gcgttaaggt cgaatacgcc ctcaatatcc   35880
tggctgtaca tgttttgctc atcgtcaaat gtgacgttgc aagtagtgta catgcttttt   35940
tcacttgcga acgtataggc aaatgagccg tcaacgacgt tgtcgttagt gaaaatataa   36000
gacgactctc gcggtcggtc gatgacaatt gaaaggctct cgccgttcca gaagctcatc   36060
cctcggaata ttgagcaaat atctcgaacc agattgtaag cctcaacctg agactggatt   36120
accacgtcgc aaaggtagcg aggctccaaa cctccgtgac cgtcaggaac tttctgatcg   36180
cagtattgac cagcatcata tagcgaccac ttatcgaccg cgatccctag ttctcgttgg   36240
tcgagtccat atctctgatt ggtgatcaaa tcataaagca cccacgcggg gttatttgac   36300
catgcttttt taaaactccc atcccatgtg ccgctatatt cacgtagctc tgggttgtag   36360
ttgctcggaa cgttaatcaa cttccatttc tttttgtgc taatgcttgg gatctgcggg   36420
aaaagctcac tgttaaactc gacgtaaaca agaccagtca gaggataacg gaactttgca   36480
tcaataacct cggcatatga ctgaatgttt atcgtgtcaa cgacgcgcga attagttgaa   36540
tcaggagtaa cccgccgaac acgcagaagg acttgactat taaacgtcgg caagtcaata   36600
cgcttcgttt tgtcatatcc gcttagtgtt ttaccgtcga ttgtgtcaga tagaacctcc   36660
tgataactac cgccatcaac cgccatatct accgcccact tcacgaccac gcctaccata   36720
tcgccgtttt ctttcgtggt aacgccgcga ggcatcagga ttttttactcg aacggctgat   36780 agctgcttat tcgttaccga gatcacgtaa ggcgtagttg ttttcaattc acggcctaca   36840
gtgaactcag ctgccgtgtc gttaaatcct ttgatgtagt cctgtgtttg cgtgcctggg   36900
cggaactcag ccttaacgcc ttcatagtta acctctccag aaggtgcaat tacaggaacg   36960
tcattaagat ataaatcctt taatgaaaaa ctctcatcaa cttccacgtc actaactgcg   37020
agcaaaacct taatcttgtt gattgaaatc aggttatctt ccatctcctg tggggtatga   37080
ggcttactgc ttccacccct tctgcctgtc actacactat ttttaatcat gatgtttagc   37140
ctttcgtgcg atttatagaa gattcattat acaggcgtaa aaaaacccgc gcaaggcggg   37200
ccttaagtta tgccatatct tcggcgacgc tataggcgga aaaggtcgcc ccgcctaccg   37260
tcctgtaccc atacgggacc gggatcgggt ttccagctgc cgttgtgtta actgcgccac   37320
cgaaagcgta tgaaggcttg ttttttgctgc tctgaacctc catctttgat cctccttgct   37380
gtggtgaaat catctgcatc acaccgccaa ggaccattgc gccgcccatc ataaatgctg   37440
atgttgcgaa tgtacccata agagccagtg acgcgccacc agtgtagaat gctgctacca   37500
tcatcactgc accgacaaca atctggaaca taccaccatt ttttgaaccg gtagggatcg   37560
```

```
gtataattct cacctccttc gcgcagctga atgccgattc atcatgtggc ccaacatttt    37620
taccatcaac gaaaacagcg aagttcatac gagagccgac ctcgctttgc atgaactcct    37680
tgaatcctgc aacctgagat gacaacgctc tgatcgcttc tgggtatgat tcaacatcat    37740
atttgtggaa aacgccgaac ctgcggccca gcgatcctga tagcttgatt gtctttaaca    37800
tttctccaac tccttatgcc tacaaaccat tactgtgtgt tcctggaacc agcctgagta    37860
aatgtctgtc tttgacagct taccaaatgc gtgatgtagg agttgattat tgccaaggta    37920
aatccccgca tggttccata catcagcttg taatttcatg ataatcatgt caccaggctc    37980
aggatctttt ccggttttaa caaagccctc tttaatgtag ttgtcctggt agaggttctc    38040
accatattca ggcttccacc actcgtaagg ctttcggaag tcattcagga ttactccgtg    38100
ctctttgtgc catgccataa ccagtcccca gcaatcgaaa gagccaagcg accaaggccg    38160
accaatcaga ggcatagctt caggatgaac aattctcata tcgccttccg gcaggcttac    38220
aataacccat ggcaactcca tctcgttcaa tacgcacagg tcgtgagcgc ttggtaacgt    38280
ggtggccccg tctccagtgt ggctatgaac aatggcaatc gtggttaggt ccgcgttatc    38340
ctcaatgctg gcgtattgca cggggtcaag ctggaatcct ttttccggtt cagagtgaac    38400
gttgtcaact ggccagaatt tctgaacccg cccctttttga gtgaccactc cgcaacattc    38460
attggggtat actgatttcg catgttcgaa gattgccatc ttaattttgc cgttaatcat    38520
tggtttttcc tgtcaagtga tgcgaccgca cagccgccga atctaattc gttttttgtcg    38580
ccaaatcgta atttgcaggc cgttaccgtt cccgcgcata cgtcctgtga tggattattt    38640
actgattgt tgtctttgtc aaacatccgg ctaccattat aaccgcaacc gcgtccgctc    38700
cgataccatc cacgctgcgc ccaaaagcaa acactctgag taactcgcgg tgggatcatg    38760
atgccatcca tatcgtacgg tgatgtcagg tcgaatctcg caaggttctg atccacaaag    38820
ttcggtcgct caacgtagta aacgtatttt cggaagtcgc cagccgcaac gtttcctgta    38880
ctgccaagca tttcgcgtga ggttatccag atagtcacct tcgcctgcat catgccgttg    38940
taggaccgga taagcgccga tacgcgacta tcaaggtttg atagcgataa ctgaggcttt    39000
ccggccttgc catttccatt taagtcaatg ccagagatgc cgaaaggacg tgcgccatat    39060
tcatttccct gaaaggtaat tgttttttggc tttaggctcc cgcctggctg agttgctgcg    39120
agaatttcct ccggcgtgaa ctgaatgttc cgttgtgga atcggtagac ctgcgcgccg    39180
aatttcgttc cgtcaacgtc gattagcgtc atgatctcac cagggaatag cccctgcaat    39240
acgttttcaa acttaggtgt catgggatta cctccaataa aaaagccccc gttaggaggc    39300
tttattctac accgctgtga aggcttctac aatggtgcat tttacaacaa gaagaccacg    39360
accgattggc tgagtattca gcgtgtccgg cttcaatagg aagacgccga tcttgtcctc    39420
cggtggggta aaggcaaagg ctttcagtct atgcgatcgc aaaaactcgc gcacttcttt    39480
ccagtccttg ccaacgtaac tgattgcgta ctctcgtcgc tcagtgttat agccagacga    39540
tgcaacctgg cggaatccat tgccaaactg cacctgcctg tcattgttag tgacggtcat    39600
tacaccgcca ccatcctgaa cctgtacgca ccacttgaac acgtctaggg ccatttatta    39660
cgctcctgct tttccgttga tgtaattgta aacttcgcca ccctgggaac atgattcctg    39720
aatcatttgc ttgaaaatca ttttcacgcc ttgctccata cccttcggat cgctaccgtt    39780
attgatgcta acagggatgc ttccaattgt cacgccgcca gccatgattg caccgctgcc    39840
gccaccgctt gaagttccac caaccatccc gccattcgca taacctcgca tcattcgata    39900
aaggttatcg acgccaattc gcttggtagc ttccttggtc atgacaaatt caccttatg    39960
```

```
aactgtgccc gctggctcat actttccgcc gtctccggta tatccgccag tggcgaacca    40020
tcctgagtta gcgaatgaga accccttacc gctgccaccg cccatcatac ctgacagtga    40080
gttaaagatt accatctgcg tgatcatctt aataatctgg ctgataatac tctttgcaaa    40140
gtcggcaaag ttggcctggc ccgtcatcaa gaactcagtc atcatgtcag acaaaccgtt    40200
cagggcgtta gctgcgatgt tgcctacgtt ggtgtacata tccgttgcgc tttcgccgta    40260
gtcttcaaat gcacgttgcg cgcctgcaag ccagtctccg cgtttctcat cctcgttggc    40320
gtaatactcg ttctgcttgt caatcatttt cttgagagct tcatcatcct gaccgccgcc    40380
cttagacatg taatccgctc ggatcttctc aagctgaatc tggcgttctg cctcaagtgt    40440
acccatggcg cgcgtggcgt taaggctttt gctcgctgcg tcaatttgca tgatgaactt    40500
cattgattcg tcattcagtt tgttgatctg ctcctgctta acaatctgat caccaagctc    40560
tgctttctcc ttcgctaacg aaagcacctt ttgctgactg gctagcaatg cttttcctc    40620 gttggtcagc ttgcgcttac tctgtgcatc ctggaggatt gaaatctgag cctctgtagc    40680
ccacaaagca cggcgctgtg ttgagatctt gtcgttaatc gacttgtgat cttctaaaac    40740
tttaagctga gctttgagaa cgtaaagttc tttatcaagc tgttccgtag cgcccttggt    40800
tactgcgccg ctgctcttag ttttcttcct gttctgctct tcaatggctt tcgcttcctt    40860
ctctacagcc tcctttgtct ccttgctgta ttgcttctcc atatcgcgtc ggttcttgag    40920
agcgttgatg taacccattt cgcccttttc tactcgcgcg ttaatcacgt ccagatcttt    40980
tgcgaggctg tcataggtgt ctttggagtt cttaacgata gtctgctgtt cgttgagaat    41040
atccttaccg aaatcactca taccaggcag gctttgcgtt gccttgattg ctgaggcaat    41100
aaagttagaa atgtactcgt caccttggc gagaatcatt tttacctgaa tcaccgtacc    41160
gctaaccacg tcaattatga ggtttagagc accaagcgta tgatcgccaa cccacccca    41220 ggcgtcggat gaccatttct taatgtcggt ccacatttc tcaagcggcg ttgcagtacc    41280
tgcaatcttg ctcatgcgtt cttccatggt gtcagcaaac agctttgtcg cctccgtcac    41340
ggcttcggtt tcgcccttgg ttttaacaat cccgttgata taggtcagtt ggcctttctc    41400
caggaagttg tattgctcat tcagcttcgc aagccctttt accggatcat ctgcaatctt    41460
gccaaagtca ctgatgatgt cgctcgtagc tcggcccgtt gcggctgacc attcagcggt    41520
ggcgcgggtg atattcctga tttggtcctg agtgtactta ccgcttttg caagctcagt    41580 ggcaatttct cgcacagatc cgatagtcgc gttgctggtg tctgcaattt tgtttgcgat    41640
cgcgtcaagg tcctcagccg tagccgctgc aaatccacca gtttcaatca aggcgttttg    41700
catatcagta atgtaacggt aggagtcata accagctttt gccaggccag caagagcaat    41760
acccatcgca gtcattccaa cggtaactgg attcaggtat gaagaagaa ccttgaacgt     41820 gttgcctacg ccgccgaatg aatccttgat ctgcccaccc tgctgaacag ccaccaacca    41880
cacaggcata cctgacgcaa gagaagtaac cacgtcagtt atctgagctg gtagcatacg    41940
cattgcgttt ttgtactcac caacagaaag cccagcgacg tttgtagcct ttgcctgctt    42000
attcattgcg gcgataaatg gagcggcctg agtcgatacg ccaagctgtg ctgccttcaa    42060
ttcgagaagc tcggtcttgg tcattgtcgc ggcgttagct tgttcttgca gtgatttaag    42120
gaatctgtca gcgtcctttg ttgccgcctc tttggccttt gagttagcta gcgccgcacg    42180
accttcttcg gtcagcgcca tcttggagcg gttaagtgca ttgatctgag tttcaatcat    42240
gcttgacaga ttgaagaact cggcgtctgg aactaggcct ttgctccata ggttatccag    42300
```

```
gtcaacgctc gccttctgca aatggcgcat ttttccgatt gtaggatcga tagctttctc    42360
tacgtcggca aactctttct tctggcgctt cacctcgtta ttgaactctt tcattttctg    42420
ctttgcgact tgctcggcat caatgaaatt gtcaaagctc tttccggctg tgttgtttgc    42480
cctggataag tcatccagag atttaacagc cgcgtcaacc tgggatacgt caaccccaag    42540
cgatagccct gcaaatttat ctgtcataaa accccatac gaaaaagcg cccgtaggcg      42600
ctattatttt ttgtgcattt gcttaagcgc ttccgcttcc atcacacgca catcatttaa    42660
ggccatttct tcacaatcta ttttatagat tcgaaatagc ataggcaaga cattataatc    42720
aagcccgtaa gctccggctc cggcagacct ccattgagtt tgcattgcgg tgaatacttc    42780
ccatgactgg taagtttcct cgtcgaactg caatatctct ggatcttcgt tgtcgtagtc    42840
ctcacgggtt aatccgtatg cctcaagttc tgcgtcggtg ggcgttcgcc tgaatagtag    42900
ctcgaccgcc cgttttagtt ttttactcgg tagccagcca gcgcttgagt gtaagttgag    42960
atcaggccgc caacaacggc agggtaacta tcaacaagct tattgatgtt ttcatcattg    43020
aactcgtcct caagttccca cccactagcc agggatttta caaactgagc tccagtctgt    43080
ttttctgcat ttttcagcgt ggcgttaagc tcggatgacg ttagcgcctt gacagtgaat    43140
gcaaatgtag cttcaacgcc gttcggcaat acgaatttaa ccggaagtgg gaagtccggc    43200
aggcgttcag atagggttac tttaaagctc atagtgtttt cctctttgtt tgaattggtg    43260
atattaaatc acaaatagaa aaaggggggca atagccccct tgaattacgc agattctttc   43320
atgtgcgtgt atttgccatc aagtgagatg gtcaggatgg tcgtttcatc ttcgttcatc    43380
actgtgttag ggatgtcatc gaaagatggc gtaccagaga aggtgcggat cggatagctt    43440
gcctttggta cgaacattcg cattgcgcgg ttttgccgt cttcgtcgta accaatcaga     43500
agctgagtga ttgggttgga gtagtcgaag tcgaacgtat acgcgatgga cgtcgcagat    43560
ttaaaggtcg ggatctgctt ctctcggtca tctgaaagac actgcttggt atagaactgc    43620
tgctcgccgc cagattttgc aatgtcgctc acgcatggaa tctcaatcca gctttcgatc    43680
ttaacgaagg tggaagcgcc gccagcgggg aacttgttaa ggtcagccgt ggaagtgttc    43740
ttgtcgcctt caagcgtgat tgatgcgtcc agggttactt ctttcactcg cattacgcga    43800
tttttaaatg cagcccatac gctttccagc accaggacgt aatcgccttt cacaatgcca    43860
gtggttgacg caacagtcgc caccggattt tccgcgttac tcactgcggt tgcttcgatt    43920
tcggtggctg ctcgggtctg ctcaataaag atttgggaac cgttaggaag tgccatagtt    43980
aatgctcctt tattcgtcgt attgtactgt gaagcggatt ggaattaacc agcctctttg    44040
tgatttctga acgggctttt ggctcgcgcc ttcaaaaata aaacctacag aaaggatttt    44100
accatcttcg aagaaattag caatttcttt tgccagtttg cgcgcgtcgt ccatgccagt    44160
atcaggagaa aaaacaatac caatctggac aaggccacga atcctgacac acttccggct    44220
caaagatttg tacgtcttct ctgccggaat gtaatcaaac ttcaaccacg tagagccatc    44280
attaggctct ttgaatggca cgttctcata catgatcggg aatcgactac caaactcacc    44340
atgcagcgcc ttacgcgccg cgaccgctag gtcataatcg tcataaacca tttttattcc    44400
ttgattcaat aattgccgct gatatgtaag aacgcaaccg gatagccacc aggccaagca    44460
caccagcggg cgcttgctgt gaatgtccgt actccagagc atttgcatag atcagcatgt    44520
tagaaaaata gatggtagtt accgccccgc cacggcctaa cggcaatgcg ttagcagttc    44580
gtacacctgc ggctatggtt ttacttcctg acttatcata ctcattcagc gcgtacattg    44640
gaatgtgatt ataggttatc tgccagttag ctctaaatcg acccgtatca actggtgagc    44700
```

```
ctttgactaa atcggcgtgt acagccttga cgaactcacg aataacgtca tcaaggccag   44760
attttacctg cttaatccac ttctctatat cgccctggaa tttcctgacg atatagttag   44820
ccatgcgccg ctaccttacg caaaatagga cggtatgcga taacgtgaga ttgagtcggg   44880
ttaactggtc gattgtcaac gacgcgccag tgctggccct caaggatgat aatcatcccg   44940
ttctcgatcg gtgtaacgtt agagaagaat gcccgcttgt cgcccagctt gatagattcg   45000
ccatcaatca tgtgatagct gatcgctcgc acagcgccga acactttacc gcgaacctcc   45060
ggcactttca cttcttcgcc gtcaaccatt ggacgccgc caccagtgat gataatgtcg   45120
aacccgacct catcgttacc agaaaaggca ttgattccct gatcggtaag cctttggatt   45180
tcattataat caatcatcgc acgcacccc gcgtccgtat gccagagata aggccgaagc   45240
caccgccttt cttcttgtta agaacgtcga acatcttacc ccatggggtt tgtgtaatct   45300
gacgcccgtc agtgttctga gttacagagc cgtagccagt ggaaaattca ccgctcaggg   45360
agaatgacgt tactcgccga gagtagttct ccagactttc attctcgccc ttcattgcac   45420
catccaaaaa cattaagtgc atggtgtaca gggatagcgc tttgtaatag tcagcaccga   45480
atttattctt gcacacgaag gactcagcca gcatcatcca cgcaaggaag gtgacgctat   45540
caacctttcg taacgctggg gccaactggc acataaactc gaacgcctta atctgatctt   45600
cattcatagt agcttcctca tgttaaaaaa aagggacgca tcagcgcccc tataggttat   45660
ttgtattcct tgccagtttc aagatcttca atatctttca cttcttttc cggcttaacc   45720 ttcgcggcct ttttgatttc ggcgatgtac tcacgcgtgc gtttcggatc gtcttcaaat   45780
tcaatgtctt tacgcaagaa caggtatttc aacgcctggg atttgatttg ttcctctgtt   45840
acttccagag tgtcatcagg ttttatatct tgcttttcga tacgaaccag acaagcgccg   45900
atgttcttaa tgacgttttt cttagccatg tttatttcct tttgattagt tttaacgagt   45960
gtattgccta ggtgttcaat gtaattgttt tgatgttgca tgtcaataaa aaaagcccct   46020
gacgttaatc aggagctttg tcttacttac ctacgccaac cagcatgata attgtcagag   46080
gacgatatac gatcaggcca gtggtcttgg aggtgcacgg gactttgaaa tgcaaatcct   46140
tcgcctgcat cggcagcatg ttgaaagact caggaatctc gatgctcatg ttcatcgggt   46200
ctttctcata cgccagtaca gctttcgtgc ctgctccgtc gatgtcttcc agttcagaga   46260
tggaagagat ggtgatgcca ccgttctgag acttgaacca gtccagataa ctcatcgtgg   46320
tttccggcat acgcttagcg agcaatttac gctgggacgg cgggataacg atgtcggtga   46380
ttttgtgctg accattggtc agggtttcca tcttctcgat caggtcggtc agttcttcgc   46440
ttgctttctc tgcgtcagcc catgcgccag tggcagaggt tacacgggtg atgttcggat   46500
ggtcgaaaac agagatgatt ttgtgaggct tggagccttt gaaaaccaac tggttaacca   46560
gagtttcgtg accttcacgc gccagtgtcg ctttacgatc cgacaggctt gaacccaatg   46620
ctgcaccagt cttgatttcg tcgatagaaa tcaaccacgc gttaccgagt cggtgaactc   46680
gaccagattc caggctgtga gttgcgtcaa cagtcggcag gtcgtcggtg tagtcagcga   46740
taatcttcgc catggtcacg ccgtcaaact tgagatattc gaacaggtta gcggtcgggc   46800
taatctcagt ggtgacaggg aacagggcca gagcggaagt tcagggtaa gccgcttcat   46860 actggcgctt aagtaactga gtcatctgct taacggtcca gataccaagc tgatcggcct   46920
tgttgccact tacgccaagc tggcgcatac cgttagtaat catgttctgc tcgaaagcgt   46980
cgagtttcat agtcataatt tgttttcctt tgtttgttag aaagccgtga ttaagttcac   47040
```

```
ggctctataa tagcattttt tgttaaacgg tcaacagctt tttatgttaa gcgattatgt   47100
cgttctctgg caataaaaaa ggagcctttc ggctccctat tatggttcag atattaagct   47160
gccggacttg ccggaagctg aattgagct tgagtaacct ggattttgat aatgtcgaag    47220
ttctcatcat cagtctttag ccactcgccg gtggtggtgt aaacagtgcc aatgccagtt   47280
gccgccacag tacccgaagt ggtcaagaat acctgcttat tgaactcttt gttcacttct   47340
ggcaggtctt tagcacacag tacccatgcg cgaccatttg tcagtacgtt gattgcagaa   47400
ccttcgtcat aagcaccatc cggagagtat gcgtgagaca tgatggctac gcccaccagg   47460
ttcggagttt ctgccgagat ggtgtcagtt acgactttgt gaccatcaac aacctttccg   47520
gtagggtcga gggcgactac cacgccagcc ttaatttctt tagccgctgc acaagcgcca   47580
tcaacgttgt agagagaagt gtcagccagc aggcctgcat atgcttttga acggttaacc   47640
gtataagatg ctttgattag tgccatgata ttttttcctt tcacttagaa tactaagcgg   47700
cctttagacc gccatttat tacttacgga agcgagcctg tggatcagga atcgcgtcat    47760
tatctttgtc gccctgagcg ccgtcggctt tgtcgccgtg cactttaatg cgttgagcag   47820
ccatcttatc agaatcgcgc gcgatttcat aagactgatt gatgtatgcg tcggattttt   47880
ctttagcgtc aatgccgaga acttcgtcaa taactgccag cttgatagct ttctcatcca   47940
ggccgtcgca cttgatgcca aggccggaag cgaaagtgag aacagcgccc agcgcgtcag   48000 cttttcttt tgcatctgcc agagcggctt caatctgtgc cggaatgccg tcaacctttg    48060
cttgcagcgc gtcgcgctca gcttgcaggc catcgacttt agcgccagct tgttctgctg   48120
cgttttgcag tttgccgatg tggtcagcta cgtctttgga cacttccact ctgcggaat    48180 caattttgat ttttacggtc atgttacttt cctcattggt taattgaaca tgctcatcat   48240
atttaatttc ttctgagccg tcaaggttta atctggcaat acctgcgcgc cctttactca   48300
ctagcgctac gtgattaacc cttatttag tttgtaggac atcaaactca acccagtcat    48360
ctggaatggt tatgtcaggc tccatatcct ctttaagaat atattgacct gaaacattcg   48420
atccccaacc ctccttatga atctcaataa ccgtataacc tactgacaac tcccttgcct   48480
caccgctctc agctgcagca atcgcagcag agtccattat agtgatcggg cacatcacct   48540
tcccctcgct tctgtcagcg aaagcctctc cggagcagtt gccaacaaca acatcttttg   48600
cattatctgg cgttaccgtt acgtgaccaa gcgtgacagg ctttcctctg tagctagcca   48660
gtgaaacgaa atcaaaaact tcactttctg gcctaaattc cctctgaatt gccccgtcag   48720
ctagcgtgta ctcctgcaaa ccgacccttg caaccactgg tacgtcaaca agaaatccat   48780
tttcatcctt tttcgccttg aataataggt aatcaaatct ttgctttgcc ttcatacact   48840
aaccctctcc aaatccagtt aatttaaaca tccaattttt cctcattaat catgatattt   48900
ccccatttgc tgttgtgaag tccggaactg cccaacaacg gcatccgtaa ggttccccag   48960
ggaaagggtg atcacttgag atctcaatac gtttaccttc ccattttacg tgctgcaatc   49020
gctcgcgctc gtccagttta ccatgccaga aatagtgagt tactccagca tcatccagcc   49080
gctggcgcat cagtacgctg ttccatgtgg acacgattcc acgtgagcga ttcacggtcc   49140
agccagtata caccttgtag cgctgcttta aaacttcatc aatctgctga ctggttttat   49200
tgcgcacgtt ttcgacgcgt aggttttgcg accagtcaga gatgatgtcg ttcgatagct   49260
ttagaatact cacctcagcc gaaccgcgcc attgcgatga cttctcgcga taccatgact   49320
cattggtatt cgcccaagc gcgccaagca agatcacaga ctgattttt ccgccaccag     49380 ccttttttcgc cacgttgagg aattgccttg agttaaactt gtagatagtc agagccagcg   49440
```

| | | | | | |
|---|---|---|---|---|---|
| ccggaagtgt | ggcaacaatc | gccgcgataa | gtcctgctgc | gtattcctca | agctcacttt | 49500 |
| ctgcatcatt | gatttcttcg | tccgaagcgt | caaacctcat | tcctcccgta | agcgatctgg | 49560 |
| ctttctttgc | catctcgcct | gcgaaggttg | acaatgagcg | gctaagctgc | cgctcgcttg | 49620 |
| cttcgggata | actccattga | tttacaatgc | cgttaacctt | catgatcatt | cctcgttgct | 49680 |
| cacctgcggg | ttaattggtt | cgacttcaag | ctcaggcgct | ggtccttgaa | tcttgataaa | 49740 |
| gtctgcgatc | gcctcaagtg | tatcacgcgc | ctcatcgcgg | tcaataatct | gatccgcaat | 49800 |
| cagctttgag | attgactcaa | cgttattctt | caaagtctcg | gattgctctt | tctcgcttgg | 49860 |
| cattgatagc | ggctcaaagc | ggattgacca | ttcatcttcc | tgaataatca | taggaaccag | 49920 |
| ccactcaaga | agaggcctgt | aatactcgtt | acgcttgcga | tcaatcatct | tatagaaagt | 49980 |
| ctcaagcgcc | gtattctggc | tcgctgacac | gcctcctacg | ttcttattct | tgaggataat | 50040 |
| ctcatgaatc | tgtgagtagt | tcacgatgcg | gtccatcttc | ttatcaagga | aagcatcaac | 50100 |
| gccgccaatg | tcagagttaa | gaacgtcgta | ttcttcgtcg | gttgcatcaa | tgccgatcgt | 50160 |
| ccggcctacg | ccgctattgt | catcaacctg | cgctaatcgc | agtcgcgccg | cgtaacgccc | 50220 |
| ttcgtcatcg | tcgcacaaat | ccgccagacc | tttagctttc | catacgcctt | gctgcttacg | 50280 |
| gcgcaatagc | tgagtcgcca | gttcctcaca | gtagttgtag | tcaagaatgg | catcaatcaa | 50340 |
| gcccttactc | agtacagatg | ctcccccaatc | gttattctgc | gcgcgaagtg | agccagggac | 50400 |
| acgctcgcct | ccgttaacat | agattcgcgt | gtagtgaacg | tcgtattccg | gtacgctgcc | 50460 |
| gccagggtta | atggtgtaaa | tcttcggcat | accatagcga | gggttgcgtg | cgttcttctc | 50520 |
| gcggtccttg | atgcggatct | gctctttt | | | | 50547 |

<210> SEQ ID NO 2
<211> LENGTH: 8358
<212> TYPE: DNA
<213> ORGANISM: Artificial Sequence
<220> FEATURE:
<223> OTHER INFORMATION: Novel Bacteriophage CJ24

<400> SEQUENCE: 2

| | | | | | |
|---|---|---|---|---|---|
| caccattggc | agcgtatcta | gaatagcact | tccggcaact | ggattttaac | tcgttacacc | 60 |
| ccaaatctgg | taggggcgtc | cagcaagtct | catctggtac | ttacgccgtc | gtatggttac | 120 |
| gacttacccc | cataatcttt | ctaattcaaa | gtagcactgc | tccatgtttg | gcctttgaac | 180 |
| tccgggatcg | gattagtgca | atgctacttt | gaattggtta | ccagtgaggg | attcgaaccc | 240 |
| ccggttggag | tctatagctt | accgcagcag | ctctccaatc | tagcggtgtc | acacttagtc | 300 |
| caaacttgaa | catatcaagc | catctcgtgc | aactgataat | tggttccggc | gtctggactc | 360 |
| gaaccagaac | acttatgccg | tgcacgacac | tagtacctac | accggaatta | attgccaggg | 420 |
| attccacctg | gctccatctg | cttttttatag | tcactcagat | atcgtctgga | ctgtaggcat | 480 |
| gggtgggaat | cgaacccaca | aaccattcag | cactgtagcc | tcacgctcta | cctatttgag | 540 |
| ctatcacaca | ccattgatta | actccccgtt | tctaatacac | ggacgaggac | actccatggt | 600 |
| cgtttgataa | tcaggacgac | tcactcccga | ctgacgcttg | gcttattagg | ctgccatcag | 660 |
| aacaacatca | tcgtttgcat | ttatgttatt | ggttcgtttc | taaaaaaccg | cataatcgct | 720 |
| tacgaaaact | atcaaagagt | acactaagca | caggtagcta | ccctgccgtc | ttctccacct | 780 |
| acaccagcta | tagtgtaaac | ctccgcacgt | tagcttaatg | tactcattga | taggatgtca | 840 |
| gtaggtcggg | ggctggattc | gaaccagcga | gagaagtagc | gaccatctgc | acatgcctac | 900 |

```
gtgctacctc gaccattata ataggaggga ggggacgagt cctcccttta tacctatat   960 tgcatgtaag acctaacaat tcgatgctgt aggtagctat gctatccgac atttaaccca  1020
gcccatatag gggcttatgt gattaaaatg ctcaacattg agaggttagt ttgataaggg  1080
atctgaagcc ttatcccaaa gatactaacc tttgggatat agcctatcat tcagaaatgg  1140
cccctatagg gagaggccat tgattaaccc gaatgttgct ttacattttc tgtgataacc  1200
cattcttaaa atagtctacc tgacggatgg gcataaaccc tagcgtcagt gccatacggc  1260
aaagattaag ataagaaagg ttatgatagg agttcctatc tcaaaggatt ctaacagaac  1320
ccttcacgat attaactact ctttttaat gcttctactt caccttcttt ataccaagca   1380
tacggtacta agattttgca tccttccgat tcaatgtgaa atgctttctt tccttcaacg  1440
ggttctccac ccatgaaaga actaaccttt ccattgagcc agtgaatagt aaatttgttc  1500
atattagcct cagttgaacc aatgcacagg ggagagtatt cctgcacact ggttcggttg  1560
ttgttactct ggcggcttgt caccaccgtg tttaccactg catttccaca ggataatgac  1620
agtgatgata aaagctatgt atggagccga cacgtctata atcctgacca gtagtagcat  1680
caggactata aacactacca cacctagcag cagcttctga gccacctacc agattaacta  1740
cgtttaaggc cagcgaacag tgaaggctta gtagcaggt tctctgctgg ttcttcagcc   1800
ttagcctctt cctgcacaac ttcttcttgt gcttctggtt cagatactgc ttcttcttca  1860
ggttccggcg tagaactctc gttctgacca ccagtagagg tctgggtttc ttctaccttt  1920
acctcttcaa ctacttcttc cggctctggt tctaccggac gatgtttagc ttcctgtggg  1980
ttcttacgag aacgacgagt tttcttctct actcccacgg gtggagtatc ttcatgaacc  2040
tcttcgttga taccaacgga agctgtaccg tctgcattga tgacaatatt gatgtcacca  2100
gcaagattga tttgatcatc gacataagcc tgtacagcag cttctacttc ggactggttc  2160
agaatgattt gcatgttatg cctttattaa attaaggagg ttttggaaag ctgggagatt  2220
tacaccagca tggattgcac cgattgcatc agctaagtgc tcattcttat tcagaagttt  2280
gcccttctta tctgtgagcc agttggcttc aggatagatg gcatgagcag cacgaatcat  2340
cgtgtcctta gatgcagttt tatcaccgac cagtgcaagt ttgttttcaa ttggggatac  2400
ttcaaagatt ggacaaccca atgcacgaaa tgcacctatt aatcctacgc atacgccata  2460
ggatttcata ccgttagcag actgagagcc tactggtact tctacgaata ctgctttagc  2520
agaccgtaac cattcctcac aaccaagaaa caaatcgtga gcggcttgta tatctttgga  2580
gttggttcga acttgtttgt tgtggtcaac ttcagtttga accagtttaa gttcgacctg  2640
ctcgaagacg ccggactcaa tgtccagcat cccacgagct aaaaccccaa ttgcggagac  2700
taatgtctgc accgacaatt gggattttca ttaacgttta ccaaacagtg atttaccacc  2760
agcaggagca gtaccgtgc cagcacctgc acctggtttt aggaggcaag ccacctttac   2820
cattaccacc agcagaactc ttagtcttgt cacgagtttt gcctttgttc ttttccagcc  2880
atgctgcata gaatacagcc agttctgggg ttagttcttt ttcagccttc tctgcttcct  2940
gagcctcgac gactgtgacc agcagttccg ggtgaaacac tttctgaatc tcgtttactt  3000
cacgagtttc gtcagagtct acataaccgt tgtcgccttt aacctgcttg ttttccagaa  3060 cttttttccag agcgaaggta acagtctggc ctaccaggtc aactggaacc atgacagatt  3120
tattaacttc tgctttagcg tcgtagtcgt agactttaac aatcttctct tcgaagtctg  3180
cttcaggcag ttcagtacca gtagccatca gcatcatgtc gttaatgaca gtgtagccag  3240
gcaggaagta ctctttacca ttttttctcgt aagtcggctt gttgccttta gcattaccag  3300
```

```
aagtgaagta cacctgagca cggaactcgc cagcaggcac gccatcagag ttttcaggt   3360
cttcaataat taactgtatc cagtctgcac cagaatcagc tttgcctacg taagctactt   3420
ttacagtatc ggtgtagata tcggtttctt ttgcaccgaa gccaccgcca cccagagagt   3480
ctttagcagc ttcaacgttt ttggttttt cttttcagatt actgaacaat gacatatgat    3540
tttcctaata agtgattaac aaccagacaa acgcttaagc gtagtattca gccaggtggt   3600
ctaagagttt ctgggcatcg ttatcaatgt aagtctcgga cttatcgaac atacccatag   3660
gagaacgaag tcgtttacca acagacttct tggttggacg ggtctggaat acatgtttat   3720
agcctaaatc acgttcttcc tccgtaattt caagcatctt gtttccatac ttctccagtt   3780
ctttaatgtc tacacgttct gcgtaaacca ctgtagagaa gtaggcttca agcccgttat   3840
tcttcagaga gcctttcact gggatgaacg ttttcatcac accagcagct tcatccagtt   3900
cgtctttagc atgagcagta atgattactg gcttaccaaa cttaacgact ttttgttgca   3960
gcagtatctt aaagaactgt gcaaaatccc cccatgcctt ttgcgtgttt gcagaaggca   4020
gaacatactg ggattccagc atatccatca taaaagttgc tgagtcaatg atgataccat   4080
caacatcatc tgccatttct ccaccagaag atgcaacatc aaatgcttcc cagatttggt   4140
atgggtcttc gatgttgtag gtattgaact tgttacggaa aggtagacgt ttacctgcct   4200
cagtgttcag atagagccag cgttcctggt tcctgatgtt acgcagtgat gctgatttac   4260
cactcgctga gaatcctgca atcaggatta gctgagtgtt catatcattg ggaattactt   4320
cggacattat ttttcctcat ttaatttagg agtccttcaa accaaagaaa gactcctgtt   4380
tgcttatttg ccagcgaagc gtttagccac ggtgaccatt acggttgcat tcaattcatc   4440
atctggtaat ggattagcca gtttcttatt gaatgagtgg acggcttgct gtacttgggc   4500
aaaatcccaa ccactgtcaa ccaatgccag tgcgtactta atcatttgat tattacgatt   4560
accggtagca atacgactag cgaaccaacg ctccagatta tccaacgact gtacttcctt   4620
catctggttc tggaactgct cgttcttact agtacgagga ataaagtcac gcacgtccaa   4680
cagatttgct tcaagattgt aatgatagga accagtctca caggacatcc atttcttggc   4740
tcgctggtta gcagattcat ccgtttcgaa cggtagccaa gacataacgt tattcataaa   4800
ctctttgtat tcctcagtgt cgaggtgtaa ctcatagttc attggaataa tcagtcggaa   4860
gcggttctct tcatcagaat gacgtttagt ggtataggtc atgaacttat attccttcat   4920
cagttcatgg cacgtatgca gtggtactcc accatcacag tcaataacaa tcatgttaaa   4980
tcctggaata acgttctctt cggaacgatg cccgttcttc atgtgatggt ttacccagtg   5040
cataccggga gcttgggtta atacatgcaa ctggtcgaac ggtacacgtt caccaatgta   5100
gtcataagca aagctatcac tataggccac tatcatctca ttgatgtcag tctctttcag   5160
agtctctcca cggaagaact caataccttc attaaaagtt ttcttaatga tgatgtgctg   5220
tttgtatccc catgctgtag caagagtcat catctcatta cgagctgcat tgccactctt   5280
atagaacggc aacgactcca gtaagtcagc atgagtcact tctttaccta cagaagcgat   5340
atacttagcc agcttcacat aggctttctc acgattgaga ataccctgga atgctgcccc   5400
ggattcttct acaagcaaga ttgcttgttt aagatgagac atttcaatga atgaactttg   5460
gtcaacaaat gccagtgctc cagccagctt aagagcttta agtaacggt gggagatttc   5520
agccttacga atttcttcgt ggtcagccat agcttctgct tgtttctcac aatcgatctt   5580
gtaagtaatc agagcaatac ccacagcatc ttctacaacc atcttaaagc cgaacaagtt   5640
```

```
tggatcagcc agactgtgga agtgattagc ccacttaccc agagactgta cgttatcctg    5700
cttaatcagg ttacggtaga tttcttctgg ggacattgtt gcatgtgctc gtttatctaa    5760
atgcccaatg gcaaataagc aacgacgtgc ataccctgta tccagaaagt catagaactg    5820
gtcttcggtc tgaccaccat ctagtagctt acttggcgtg ccaaacagca acaggttagc    5880
tggagtctta ccatccagtt cttcaccacg aacactttca gcagtgttct tggttaactt    5940
ctgtttaacc ttaccctggt catataattc caggaacaga gttaatacat ccgtgttagc    6000
caacaggttt gaaccaattt catcaatctg taggttgatt gaaccacacc cagccattaa    6060
cagcttatgt cgtagctgtt taactgctgg tggagtacca gagtcaaacg taaacggata    6120
tgctccagca cgtttatact ctgcttcgac tttatcaaac tcatcattct ggtctgtacc    6180
ttgtcgagca gcacgttcgt tagcaatctt ccataaacgg tcatttgcaa tgacgggcat    6240
ggtgtcttcc ataaaacgtt tacggaagcc agtcatgaag ccgtcttcaa taatatttac    6300
cgagtgacct ttaccgaagc cagacgttgc taatgccata gctaaatgt tgactggtaa    6360
gtcaccacgg tctttagtga caatggttgc acccatgcag gatgccattt tagccaggaa    6420
gtaggctact tcgacacgga agaatcctct gtcgttgttt tgtgtcttgt tacacagcac    6480
gtctacaatt tcttcaattg cagggtggtg agtgactccg gtcaggtcaa tactcatgat    6540
ggaaaatatc tctctctttg tttgcaaatg gacgcgacag ggcagtatag acaacgctta    6600
acctgcccct ccacgacctt gatagcaccc ttgccacctt tttcagccat gaagatacga    6660
gcagatgcca tatcgtcaaa ttttttggta cttctggctc caggtacatc taccttagaa    6720
gcatcagaga agtatttgaa ctgtggctct gttcgccaca actcctcatc agtacattca    6780
ggaatttcct cttcaggtgc attccagtac ttttcaatga ggtgaatctt ctcttctacc    6840
caacgttcag ttttctcgac agatagcaac ggaatatcct tatgcataat acgattagca    6900
ggatagttcg gattgctatt agccatgtgt ttcatgaagt cagtgaagat gtagttaata    6960
cggattacat cttcggtaat gatgtcgttg tgaatccaac gatacaagct gccttgcatc    7020
ttatgttcat catcacggga accagcaacc caggaatagg ttgaggtaga cttaaagtcc    7080
tgcaacagac cttctgttac gatgtcgaac ttaccaccga tagtccaacc cttaactatc    7140
ctggttccac gctgttcaac gtagattggg ataaggtcag ggttagcatc aaagtctgct    7200
ttggttgggt taatgactac tgcatcaatt actcgttgag gataacccaa cttttttcaat    7260
gcagtcttat gacccagctt ccaggccttc tcgatagaat catgtaaacc agtacccatt    7320
gatgtggaga cgaaatccat aacatcaatt gactggtcac taagatctac acgatgcttc    7380
atgactattt gcttaatggg cttaagcaag gtagtaacag acagatactt aggattgtct    7440
acataatcat aatcatccgt tacaagccat acagctagtg caagactaac gtcgtgtttg    7500
ttggtaagtt tcataacagt cccaattgct tattagtttt agcaaactca ccataatgag    7560
ttatagcagc ttcatcatag agaacagcag cttctcttgg gtcatctgta aaacctaatg    7620
taattggttt actgttaacc caaatagttg ctctgtattt acctaaattc tttgaaaagg    7680
ataccccctt aaatccagat gtgtttgttt tagataaaac agcactctgg ttattctgct    7740
tgtgggtcgc ttctctgagg ttatctatcc agttgtgatg gcgaatattg tccttatggt    7800
caattctatc cgtaggccat acaccgtgca catagaacca tgcaaggata tgcccatagt    7860
acaacacact atccacacgg agttgaacgt aaccactctt cattaggtaa ccagatacct    7920
ttccggtatt cctacgagta aaaatcccgg aaataggggtc ataactaaca agctgtaaaa    7980
gcctgtcatg ggcaatcctc tgtttcataa ttagttactc gtcatgcaat agccatacag    8040
```

```
ccagagccag tgagacatca tgattgttgg ttatcttcat tagtaagtaa tcctgtatct    8100
gtgaacccag ttccacttaa tttcacttag ctgattgaag ttatacgagc aaatttcatc    8160
tcgtttatct ttataaacaa tctcaatgaa tgaaaattct ttagtgaaat gaggtttacc    8220
attgtttgta tggtgccaat aactaccaac ggtatttaca ttcgtagcag gatccggaaa    8280
taactcacta gctaacttct ccttagcaag aatacgatta gcataatgaa ccagcttctc    8340
tgcatcgtaa acagcagt                                                  8358
```